US 10,646,122 B2

(12) United States Patent
McCaffrey et al.

(10) Patent No.: US 10,646,122 B2
(45) Date of Patent: May 12, 2020

(54) FFR CATHETER WITH COVERED DISTAL PRESSURE SENSOR AND METHOD OF MANUFACTURE

(71) Applicant: Medtronic Vascular, Inc., Santa Rosa, CA (US)

(72) Inventors: Gerry McCaffrey, Tuam (IE); Sean Ward, Dublin (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 278 days.

(21) Appl. No.: 15/581,309

(22) Filed: Apr. 28, 2017

(65) Prior Publication Data

US 2018/0310839 A1 Nov. 1, 2018

(51) Int. Cl.
*A61B 5/0215* (2006.01)
*A61B 5/00* (2006.01)
*A61B 5/02* (2006.01)

(52) U.S. Cl.
CPC ...... *A61B 5/02158* (2013.01); *A61B 5/02028* (2013.01); *A61B 5/02152* (2013.01); *A61B 5/6852* (2013.01); *A61B 5/02007* (2013.01); *A61B 5/0215* (2013.01); *A61B 2560/0406* (2013.01); *A61B 2560/0418* (2013.01); *A61B 2562/0247* (2013.01); *A61B 2562/12* (2013.01); *A61B 2562/16* (2013.01); *A61B 2562/168* (2013.01); *A61B 2562/187* (2013.01)

(58) Field of Classification Search
CPC .............. A61B 5/02158; A61B 5/6852; A61B 5/02028; A61B 2562/12; A61B 5/02007; A61B 5/0215; A61B 5/02152; A61B 2560/0406; A61B 2560/0418; A61B 2562/0247; A61B 2562/16; A61B 2562/168; A61B 2562/187

See application file for complete search history.

(56) References Cited

U.S. PATENT DOCUMENTS

| | | | |
|---|---|---|---|
| 4,718,425 A | 1/1988 | Tanaka et al. |
| 4,771,782 A | 9/1988 | Millar |
| 4,796,641 A | 1/1989 | Mills et al. |
| 4,815,472 A | 3/1989 | Wise et al. |
| 4,850,358 A | 7/1989 | Millar |

(Continued)

FOREIGN PATENT DOCUMENTS

| | | |
|---|---|---|
| DE | 102008045878 | 3/2010 |
| EP | 0263190 | 10/1986 |

(Continued)

*Primary Examiner* — Christine H Matthews
*Assistant Examiner* — Joshua Daryl D Lannu
(74) *Attorney, Agent, or Firm* — Medler Ferro Woodhouse & Mills PLLC

(57) ABSTRACT

A distal shaft for measuring pressure distally of a stenosis includes a housing, a pressure sensor, a cover, a tip, and an aperture. The pressure sensor is mounted in the housing. The cover is coupled to the housing and covers the pressure sensor. The tip is coupled to a distal end of the housing. The aperture is disposed through the tip and/or cover. The aperture is configured to allow blood flow to the pressure sensor. The cover further includes a coupling mechanism or coupling that couples the cover to the housing. The coupling mechanism may be a snap-fit mechanism, a friction-fit mechanism, and/or an adhesive.

25 Claims, 17 Drawing Sheets

(56) References Cited

U.S. PATENT DOCUMENTS

| | | | |
|---|---|---|---|
| 4,901,731 A | 2/1990 | Millar | |
| 4,924,877 A | 5/1990 | Brooks | |
| 4,928,693 A | 5/1990 | Goodin et al. | |
| 4,936,310 A | 6/1990 | Engstrom et al. | |
| 4,941,473 A | 7/1990 | Tenerz et al. | |
| 4,966,148 A | 10/1990 | Millar | |
| 4,966,156 A | 10/1990 | Perry et al. | |
| 5,029,585 A | 7/1991 | Lieber et al. | |
| 5,046,497 A | 9/1991 | Millar | |
| 5,050,297 A | 9/1991 | Metzger | |
| 5,085,223 A | 2/1992 | Lars et al. | |
| 5,125,058 A | 6/1992 | Tenerz et al. | |
| 5,195,375 A | 3/1993 | Tenerz et al. | |
| 5,267,958 A | 12/1993 | Buchbinder et al. | |
| 5,280,786 A | 1/1994 | Wlodarczyk et al. | |
| 5,427,114 A | 6/1995 | Colliver et al. | |
| 5,451,233 A | 9/1995 | Yock | |
| 5,466,222 A | 11/1995 | Ressemann et al. | |
| 5,526,820 A | 6/1996 | Khoury | |
| 5,542,434 A | 8/1996 | Imran et al. | |
| 5,564,425 A | 10/1996 | Tonokura | |
| 5,569,219 A | 10/1996 | Hakki et al. | |
| 5,573,007 A | 11/1996 | Bobo, Sr. | |
| 5,591,129 A | 1/1997 | Shoup et al. | |
| 5,637,091 A | 6/1997 | Hakky et al. | |
| RE35,648 E | 11/1997 | Tenerz et al. | |
| 5,694,946 A | 12/1997 | Tenerz et al. | |
| 5,701,905 A | 12/1997 | Esch | |
| 5,715,827 A | 2/1998 | Corl et al. | |
| 5,813,997 A | 9/1998 | Imran et al. | |
| 5,827,243 A | 10/1998 | Palestrant | |
| 5,873,835 A | 2/1999 | Hastings et al. | |
| 5,902,248 A | 5/1999 | Millar et al. | |
| 5,964,714 A | 10/1999 | Lafontaine | |
| 6,033,366 A | 3/2000 | Brockway et al. | |
| 6,056,719 A | 5/2000 | Mickley | |
| 6,089,103 A | 7/2000 | Smith | |
| 6,106,476 A * | 8/2000 | Corl | A61B 5/0215 600/486 |
| 6,106,486 A | 8/2000 | Tenerz et al. | |
| 6,112,598 A | 9/2000 | Tenerz et al. | |
| 6,142,958 A | 11/2000 | Hammarstrom et al. | |
| 6,167,763 B1 | 1/2001 | Tenerz et al. | |
| 6,182,513 B1 | 2/2001 | Stemme et al. | |
| 6,193,669 B1 | 2/2001 | Degany et al. | |
| 6,224,585 B1 | 5/2001 | Pfeiffer | |
| 6,248,083 B1 | 6/2001 | Smith et al. | |
| 6,296,615 B1 | 10/2001 | Brockway et al. | |
| 6,312,380 B1 | 11/2001 | Hoek et al. | |
| 6,336,906 B1 | 1/2002 | Hammarstrom et al. | |
| 6,354,999 B1 | 3/2002 | Dgany et al. | |
| 6,379,308 B1 | 4/2002 | Brockway et al. | |
| 6,394,986 B1 | 5/2002 | Millar | |
| 6,409,677 B1 | 6/2002 | Tulkki | |
| 6,471,656 B1 | 10/2002 | Shalman et al. | |
| 6,517,481 B2 | 2/2003 | Hoek et al. | |
| 6,546,804 B2 | 4/2003 | Stemme et al. | |
| 6,551,250 B2 | 4/2003 | Khalil | |
| 6,565,514 B2 | 5/2003 | Svanerudh et al. | |
| 6,585,660 B2 | 7/2003 | Dorando et al. | |
| 6,615,667 B2 | 9/2003 | Smith | |
| 6,659,957 B1 | 12/2003 | Vardi et al. | |
| 6,659,959 B2 | 12/2003 | Brockway et al. | |
| 6,663,570 B2 | 12/2003 | Mott et al. | |
| 6,716,178 B1 | 4/2004 | Kilpatrick et al. | |
| 6,733,459 B1 | 5/2004 | Atsumi | |
| 6,754,608 B2 | 6/2004 | Svanerudh et al. | |
| 6,767,327 B1 | 7/2004 | Corl et al. | |
| 6,821,287 B1 | 11/2004 | Jang | |
| 6,860,851 B2 | 3/2005 | Knudson | |
| 6,868,736 B2 | 3/2005 | Sawatari et al. | |
| 6,926,674 B2 | 8/2005 | Tenerz et al. | |
| 6,938,474 B2 | 9/2005 | Melvangs | |
| 6,966,890 B2 | 11/2005 | Coyle et al. | |
| 6,974,422 B1 | 12/2005 | Millar | |
| 6,976,965 B2 | 12/2005 | Corl et al. | |
| 6,993,974 B2 | 2/2006 | Tenerz et al. | |
| 6,994,695 B1 | 2/2006 | Millar | |
| 7,017,416 B1 | 3/2006 | Liu et al. | |
| 7,021,152 B2 | 4/2006 | Tenerz | |
| 7,025,727 B2 | 4/2006 | Brockway et al. | |
| 7,060,038 B2 | 6/2006 | Letort et al. | |
| 7,097,620 B2 | 8/2006 | Corl et al. | |
| 7,112,170 B2 | 9/2006 | Schock et al. | |
| 7,134,994 B2 | 11/2006 | Alpert et al. | |
| 7,137,953 B2 | 11/2006 | Eigler et al. | |
| 7,211,048 B1 | 5/2007 | Najafi et al. | |
| 7,222,539 B2 | 5/2007 | Tulkki | |
| 7,229,403 B2 | 6/2007 | Schock et al. | |
| 7,245,789 B2 | 7/2007 | Bates et al. | |
| 7,263,894 B2 | 9/2007 | Tenerz | |
| 7,274,956 B2 | 9/2007 | Mott et al. | |
| RE39,863 E | 10/2007 | Smith | |
| 7,294,117 B2 | 11/2007 | Provost-tine et al. | |
| 7,329,223 B1 | 2/2008 | Ainsworth et al. | |
| 7,331,236 B2 | 2/2008 | Smith et al. | |
| 7,343,811 B2 | 3/2008 | Tenerz et al. | |
| 7,347,822 B2 | 3/2008 | Brockway et al. | |
| 7,447,388 B2 | 11/2008 | Bates et al. | |
| 7,450,989 B2 | 11/2008 | Svanerudh | |
| 7,454,244 B2 | 11/2008 | Kassab et al. | |
| 7,458,938 B2 | 12/2008 | Patel et al. | |
| 7,472,601 B1 | 1/2009 | Tenerz et al. | |
| 7,481,774 B2 | 1/2009 | Brockway et al. | |
| 7,527,594 B2 | 5/2009 | Vardi et al. | |
| 7,532,920 B1 | 5/2009 | Ainsworth et al. | |
| 7,599,588 B2 | 10/2009 | Eberle et al. | |
| 7,645,233 B2 | 1/2010 | Tulkki et al. | |
| 7,660,492 B2 | 2/2010 | Bates et al. | |
| 7,724,148 B2 | 5/2010 | Samuelsson et al. | |
| 7,731,664 B1 | 6/2010 | Millar | |
| 7,775,988 B2 | 8/2010 | Pijls | |
| 7,783,338 B2 | 8/2010 | Ainsworth et al. | |
| 7,837,650 B1 | 11/2010 | Cox et al. | |
| 7,881,573 B2 | 2/2011 | Eberle et al. | |
| 7,931,603 B2 | 4/2011 | Von Malmborg et al. | |
| 7,946,997 B2 | 5/2011 | Hubinette | |
| 7,967,761 B2 | 6/2011 | Smith | |
| 7,967,762 B2 | 6/2011 | Corl et al. | |
| 7,998,089 B2 | 8/2011 | Smith | |
| 8,025,623 B1 | 9/2011 | Millar | |
| 8,029,447 B2 | 10/2011 | Kanz et al. | |
| 8,059,923 B2 | 11/2011 | Bates et al. | |
| 8,127,618 B1 * | 3/2012 | Zhao | A61B 5/0215 607/119 |
| 8,140,146 B2 | 3/2012 | Kim et al. | |
| 8,157,742 B2 | 4/2012 | Taylor | |
| 8,162,856 B2 | 4/2012 | Williams et al. | |
| 8,174,395 B2 | 5/2012 | Samuelsson et al. | |
| 8,187,195 B2 | 5/2012 | Tulkki | |
| 8,216,151 B2 | 7/2012 | Smith | |
| 8,231,537 B2 | 7/2012 | Ahmed et al. | |
| 8,249,815 B2 | 8/2012 | Taylor | |
| 8,277,386 B2 | 10/2012 | Ahmed et al. | |
| 8,282,565 B2 | 10/2012 | Mahapatra et al. | |
| 8,298,156 B2 | 10/2012 | Manstrom et al. | |
| 8,311,747 B2 | 11/2012 | Taylor | |
| 8,311,748 B2 | 11/2012 | Taylor et al. | |
| 8,311,750 B2 | 11/2012 | Taylor | |
| 8,315,812 B2 | 11/2012 | Taylor | |
| 8,315,813 B2 | 11/2012 | Taylor et al. | |
| 8,315,814 B2 | 11/2012 | Taylor et al. | |
| 8,317,715 B2 | 11/2012 | Belleville et al. | |
| 8,320,723 B2 | 11/2012 | Eberle et al. | |
| 8,321,150 B2 | 11/2012 | Taylor | |
| 8,410,940 B2 | 4/2013 | Samuelsson et al. | |
| 8,419,647 B2 | 4/2013 | Corl et al. | |
| 8,419,648 B2 | 4/2013 | Corl et al. | |
| 8,461,997 B2 | 6/2013 | Samuelsson et al. | |
| 8,485,985 B2 | 7/2013 | Manstrom et al. | |
| 8,556,520 B2 | 10/2013 | Elenbaas et al. | |
| 8,562,537 B2 | 10/2013 | Alpert et al. | |
| 8,636,659 B2 | 1/2014 | Alpert et al. | |
| 8,696,584 B2 | 4/2014 | Kassab | |

(56) References Cited

U.S. PATENT DOCUMENTS

| | | |
|---|---|---|
| 8,698,638 B2 | 4/2014 | Samuelsson et al. |
| 8,714,021 B2 | 5/2014 | Gamage |
| 8,797,155 B2 | 8/2014 | Huennekens et al. |
| 8,857,264 B2 | 10/2014 | Gamage |
| 8,958,863 B2 | 2/2015 | Huennekens et al. |
| 8,977,336 B2 | 3/2015 | Huennekens et al. |
| 8,998,823 B2 | 4/2015 | Manstrom et al. |
| 9,011,342 B2 | 4/2015 | Manstrom et al. |
| 9,113,843 B2 | 8/2015 | Manstrom et al. |
| 9,186,072 B2 | 11/2015 | Manstrom et al. |
| 9,220,461 B2 | 12/2015 | Samuelsson et al. |
| 9,259,161 B2 | 2/2016 | Suchecki et al. |
| 9,289,137 B2 | 3/2016 | Corl |
| 9,314,584 B1 | 4/2016 | Riley et al. |
| 9,332,916 B2 | 5/2016 | Kassab |
| 9,339,348 B2 | 5/2016 | Davies et al. |
| 2001/0051769 A1 | 12/2001 | Hoek et al. |
| 2002/0013527 A1 | 1/2002 | Hoek et al. |
| 2002/0035331 A1 | 3/2002 | Brockway et al. |
| 2002/0059827 A1 | 5/2002 | Smith |
| 2002/0065472 A1 | 5/2002 | Brockway et al. |
| 2002/0072880 A1 | 6/2002 | Svanerudh et al. |
| 2002/0157473 A1 | 10/2002 | Stemme et al. |
| 2002/0173724 A1 | 11/2002 | Dorando et al. |
| 2003/0018273 A1 | 1/2003 | Corl et al. |
| 2003/0032886 A1 | 2/2003 | Dgany et al. |
| 2003/0033095 A1 | 2/2003 | Svanerudh et al. |
| 2003/0040674 A1 | 2/2003 | Corl et al. |
| 2003/0159518 A1 | 8/2003 | Sawatari et al. |
| 2003/0163052 A1 | 8/2003 | Mott et al. |
| 2003/0176850 A1 | 9/2003 | Melvas |
| 2003/0195428 A1 | 10/2003 | Brockway et al. |
| 2003/0216621 A1 | 11/2003 | Alpert et al. |
| 2004/0067000 A1 | 4/2004 | Bates et al. |
| 2004/0082844 A1 | 4/2004 | Vardi et al. |
| 2004/0082866 A1 | 4/2004 | Mott et al. |
| 2004/0116816 A1 | 6/2004 | Tenerz et al. |
| 2004/0143240 A1 | 7/2004 | Armstrong et al. |
| 2004/0143261 A1 | 7/2004 | Hartley et al. |
| 2004/0157790 A1 | 8/2004 | Herweijer et al. |
| 2004/0162548 A1 | 8/2004 | Reiser |
| 2004/0167385 A1 | 8/2004 | Rioux et al. |
| 2004/0176790 A1 | 9/2004 | Coyle |
| 2004/0230131 A1 | 11/2004 | Kassab et al. |
| 2004/0254442 A1 | 12/2004 | Williams et al. |
| 2005/0000294 A1 | 1/2005 | Tenerz et al. |
| 2005/0011272 A1 | 1/2005 | Tenerz |
| 2005/0043670 A1 | 2/2005 | Rosenberg |
| 2005/0049451 A1 | 3/2005 | Schock et al. |
| 2005/0187487 A1 | 8/2005 | Azizkhan et al. |
| 2005/0245965 A1* | 11/2005 | Orban, III ............ A61B 17/115 606/214 |
| 2005/0268724 A1 | 12/2005 | Tenerz |
| 2005/0268725 A1 | 12/2005 | Tulkki |
| 2006/0052700 A1 | 3/2006 | Svanerudh |
| 2006/0074318 A1 | 4/2006 | Ahmed et al. |
| 2006/0094966 A1 | 5/2006 | Brockway et al. |
| 2006/0094982 A1 | 5/2006 | Corl et al. |
| 2006/0142756 A1 | 6/2006 | Davies et al. |
| 2006/0207335 A1 | 9/2006 | Tenerz et al. |
| 2006/0241505 A1 | 10/2006 | Ahmed et al. |
| 2006/0287569 A1 | 12/2006 | Schock et al. |
| 2007/0060820 A1 | 3/2007 | Lofgren et al. |
| 2007/0060822 A1 | 3/2007 | Alpert et al. |
| 2007/0078352 A1 | 4/2007 | Pijls |
| 2007/0106142 A1 | 5/2007 | Von Malmborg et al. |
| 2007/0106165 A1 | 5/2007 | Tulkki |
| 2007/0116408 A1 | 5/2007 | Eberle et al. |
| 2007/0133925 A1 | 6/2007 | Bates et al. |
| 2007/0135718 A1 | 6/2007 | Corl et al. |
| 2007/0191717 A1 | 8/2007 | Rosen et al. |
| 2007/0220986 A1 | 9/2007 | Smith et al. |
| 2007/0255144 A1 | 11/2007 | Tulkki et al. |
| 2007/0255145 A1 | 11/2007 | Smith et al. |
| 2008/0071178 A1* | 3/2008 | Greenland ............ A61B 5/0031 600/486 |
| 2008/0119739 A1 | 5/2008 | Vardi et al. |
| 2008/0119758 A1 | 5/2008 | Samuelsson et al. |
| 2008/0132806 A1 | 6/2008 | Smith |
| 2008/0139897 A1 | 6/2008 | Ainsworth et al. |
| 2008/0146993 A1 | 6/2008 | Krishna |
| 2008/0200770 A1 | 8/2008 | Hubinette |
| 2008/0255471 A1 | 10/2008 | Naghavi et al. |
| 2008/0262470 A1 | 10/2008 | Lee et al. |
| 2008/0269572 A1 | 10/2008 | Kanz et al. |
| 2009/0059727 A1 | 3/2009 | Bates et al. |
| 2009/0082678 A1 | 3/2009 | Smith |
| 2009/0088609 A1 | 4/2009 | Schmitz-Rode et al. |
| 2009/0088650 A1 | 4/2009 | Corl |
| 2009/0124880 A1 | 5/2009 | Smith |
| 2009/0125007 A1 | 5/2009 | Splinter |
| 2009/0248049 A1 | 10/2009 | Perkins |
| 2010/0014810 A1 | 1/2010 | Eberle et al. |
| 2010/0087732 A1 | 4/2010 | Eberle et al. |
| 2010/0109104 A1 | 5/2010 | Tiensuu et al. |
| 2010/0113942 A1 | 5/2010 | Eberle |
| 2010/0135111 A1 | 6/2010 | Bates et al. |
| 2010/0152607 A1 | 6/2010 | Kassab |
| 2010/0234698 A1 | 9/2010 | Manstrom et al. |
| 2010/0241008 A1 | 9/2010 | Belleville et al. |
| 2010/0280330 A1 | 11/2010 | Samuelsson et al. |
| 2010/0286536 A1 | 11/2010 | Samuelsson et al. |
| 2010/0286537 A1 | 11/2010 | Pijls |
| 2011/0004198 A1 | 1/2011 | Hoch |
| 2011/0060229 A1 | 3/2011 | Hulvershorn et al. |
| 2011/0066047 A1 | 3/2011 | Belleville et al. |
| 2011/0071407 A1 | 3/2011 | Hubinette et al. |
| 2011/0083521 A1 | 4/2011 | Hollander et al. |
| 2011/0123154 A1 | 5/2011 | Eberle et al. |
| 2011/0137140 A1 | 6/2011 | Tearney et al. |
| 2011/0178383 A1 | 7/2011 | Kassab |
| 2011/0178413 A1 | 7/2011 | Schmitt et al. |
| 2011/0178417 A1 | 7/2011 | Kassab |
| 2011/0196255 A1 | 8/2011 | Kassab |
| 2011/0245693 A1 | 10/2011 | Hastings et al. |
| 2011/0251497 A1 | 10/2011 | Corl et al. |
| 2011/0306867 A1 | 12/2011 | Gopinathan et al. |
| 2011/0319773 A1 | 12/2011 | Kanz et al. |
| 2012/0053918 A1 | 3/2012 | Taylor |
| 2012/0071782 A1 | 3/2012 | Patil et al. |
| 2012/0072190 A1 | 3/2012 | Sharma et al. |
| 2012/0101355 A1 | 4/2012 | Gopinathan et al. |
| 2012/0101369 A1 | 4/2012 | Patil et al. |
| 2012/0108943 A1 | 5/2012 | Bates et al. |
| 2012/0136244 A1 | 5/2012 | Manstrom et al. |
| 2012/0172731 A1 | 7/2012 | Smith |
| 2012/0172732 A1 | 7/2012 | Meyer |
| 2012/0203118 A1 | 8/2012 | Samuelsson et al. |
| 2012/0220836 A1 | 8/2012 | Alpert et al. |
| 2012/0220837 A1 | 8/2012 | Alpert et al. |
| 2012/0220883 A1 | 8/2012 | Manstrom et al. |
| 2012/0227505 A1 | 9/2012 | Belleville et al. |
| 2012/0271178 A1 | 10/2012 | Smith |
| 2012/0278008 A1 | 11/2012 | Davies et al. |
| 2012/0316419 A1 | 12/2012 | Chevalier |
| 2013/0015975 A1 | 1/2013 | Huennekens et al. |
| 2013/0023762 A1 | 1/2013 | Huennekens et al. |
| 2013/0023763 A1 | 1/2013 | Huennekens et al. |
| 2013/0046190 A1 | 2/2013 | Davies |
| 2013/0060133 A1 | 3/2013 | Kassab et al. |
| 2013/0090555 A1 | 4/2013 | Kassab |
| 2013/0096409 A1 | 4/2013 | Hiltner et al. |
| 2013/0109980 A1 | 5/2013 | Teo |
| 2013/0116579 A1 | 5/2013 | Svanerudh |
| 2013/0131523 A1 | 5/2013 | Suchecki et al. |
| 2013/0190633 A1 | 7/2013 | Dorando et al. |
| 2013/0303914 A1 | 11/2013 | Hiltner et al. |
| 2013/0324864 A1 | 12/2013 | Manstrom et al. |
| 2014/0024235 A1 | 1/2014 | Russell |
| 2014/0024950 A1 | 1/2014 | Hiltner et al. |
| 2014/0086461 A1 | 3/2014 | Yao et al. |
| 2014/0180140 A1 | 6/2014 | Alpert |
| 2014/0187980 A1 | 7/2014 | Burkett |

(56) References Cited

U.S. PATENT DOCUMENTS

| | | |
|---|---|---|
| 2014/0187984 A1 | 7/2014 | Burkett |
| 2014/0276142 A1 | 9/2014 | Dorando |
| 2014/0379269 A1 | 12/2014 | Schmitt |
| 2015/0032011 A1 | 1/2015 | McGowan et al. |
| 2015/0105673 A1 | 4/2015 | Gregorich |
| 2015/0112191 A1 | 4/2015 | Gilboa et al. |
| 2015/0141853 A1 | 5/2015 | Miller et al. |
| 2015/0148693 A1 | 5/2015 | Burkett |
| 2015/0157216 A1 | 6/2015 | Stigall et al. |
| 2015/0173722 A1 | 6/2015 | Huennekens et al. |
| 2015/0223707 A1 | 8/2015 | Ludoph |
| 2015/0265167 A1 | 9/2015 | McGowan et al. |
| 2015/0272449 A1 | 10/2015 | Meyer |
| 2015/0282765 A1 | 10/2015 | Goshen et al. |
| 2015/0313479 A1 | 11/2015 | Stigall et al. |
| 2015/0359438 A1* | 12/2015 | McCaffrey ........... A61B 5/0215 600/486 |
| 2015/0359439 A1 | 12/2015 | Manstrom et al. |
| 2016/0022153 A1 | 1/2016 | Dorando |
| 2016/0066802 A1 | 3/2016 | Keller |
| 2016/0081564 A1* | 3/2016 | McCaffrey ......... A61B 5/02141 600/486 |
| 2016/0106321 A1 | 4/2016 | Sharma et al. |
| 2016/0249821 A1* | 9/2016 | Boye .................... A61B 5/0215 600/424 |

FOREIGN PATENT DOCUMENTS

| | | |
|---|---|---|
| EP | 1658808 | 8/1995 |
| EP | 1260175 | 11/2002 |
| EP | 1419796 | 5/2004 |
| EP | 1493381 | 1/2005 |
| EP | 1514512 | 3/2005 |
| EP | 1702641 | 9/2006 |
| JP | 10033488 | 10/1998 |
| JP | 2000333913 | 12/2000 |
| JP | 2004-194996 | 7/2004 |
| JP | 2005095603 | 4/2005 |
| JP | 20053638066 | 4/2005 |
| JP | 20053705458 | 10/2005 |
| JP | 2006204378 | 8/2006 |
| JP | 10137199 | 5/2010 |
| NL | 2009285 | 8/2012 |
| WO | WO1997/000641 | 1/1997 |
| WO | WO1999/058059 | 11/1999 |
| WO | WO2003/022122 | 3/2003 |
| WO | WO2006/037082 | 4/2006 |
| WO | WO2006/0117154 | 11/2006 |
| WO | WO2011/0120565 | 10/2011 |
| WO | WO2011/0161212 | 12/2011 |
| WO | WO2012/093260 | 7/2012 |
| WO | WO2012/173697 | 12/2012 |
| WO | WO2013/061281 | 5/2013 |
| WO | WO2014/025255 | 2/2014 |
| WO | WO2014/176448 | 10/2014 |
| WO | WO2015/150128 | 10/2015 |
| WO | WO2016/001017 | 1/2016 |

* cited by examiner

FFR CATHETER WITH COVERED DISTAL PRESSURE SENSOR AND METHOD OF MANUFACTURE

FIELD OF THE INVENTION

The present invention relates to systems for calculating a Fractional Flow Reserve, and methods for manufacturing such systems. More particularly, the present invention relates to a distal shaft of an FFR catheter with a cover, and methods of manufacturing the covered distal shaft.

BACKGROUND OF THE INVENTION

The severity of a stenosis or lesion in a blood vessel may be assessed by obtaining proximal and distal pressure measurements relative to the given stenosis and using those measurements for calculating a value of a Fractional Flow Reserve (FFR). FFR is defined as the ratio of a first or distal pressure $P_d$ measured on the distal side of the stenosis and to a second or proximal pressure $P_a$ measured on the proximal side of the stenosis, usually within the aorta. Conventionally, a sensor is placed on a distal portion of a guidewire or FFR wire to obtain the distal pressure $P_d$, while an external pressure transducer is fluidly connected via tubing to a guide catheter for obtaining the proximal, or aortic (AO) pressure $P_a$. Calculation of the FFR value provides a stenosis specific index of the functional severity of the stenosis in order to determine whether the blockage limits blood flow within the vessel to an extent that treatment is needed. An optimal or normal value of FFR in a healthy vessel is 1.00, while values less than about 0.80 are generally deemed significant and in need of an interventional treatment. Common interventional treatment options include balloon angioplasty and/or stent implantation.

If an interventional treatment is required, the interventional device, such as a balloon catheter, is tracked over a guidewire to the site of the stenosis. Conventional FFR wires generally are not desired by clinicians to be used as guidewires for such interventional devices. Accordingly, if an interventional treatment is required, the clinician generally removes the FFR wire, inserts a conventional guidewire, and tracks the interventional device to the treatment site over the conventional guidewire.

To address this concern, efforts have been made to utilize catheters (micro-catheters) to take pressure measurements for calculating FFR. Using a catheter with a pressure sensor mounted within a distal shaft to measure the distal pressure $P_d$, a clinician may use a preferred guidewire for tracking the FFR catheter to the site of the stenosis. If an interventional treatment is required, the guidewire used with the catheter may remain in situ and the interventional device may be tracked over the existing guidewire to the site of the stenosis.

However, the pressure sensor mounted to the distal shaft of the catheter is generally exposed to provide access to the surrounding blood flow. The pressure sensor is a sensitive device and may be damaged by contact during handling or contact with tissue during advancement of the FFR catheter through the tortuous vasculature of a patient before positioning at the desired treatment site. Contact damage may result in errors in the measured distal pressure $P_d$.

While placing the pressure sensor within the distal shaft may protect the sensor from contact damage, manufacturing of the distal shaft in this configuration is difficult. For example, threading of the sensor wire though the distal shaft, mounting of the pressure sensor, and connection of the sensor wire to the pressure sensor in a confined space inside the distal shaft during manufacturing provides both build and maintenance challenges.

Additionally, as the distal shaft of the FFR catheter advances through the tortuous vasculature of the patient on its way to the desired treatment site, the distal shaft encounters bending forces as it winds its way to the targeted stenosis. When the distal shaft encounters these bending forces, the distal shaft and the pressure sensor mounted within can bend, damaging the delicate electronic pressure sensor. Bending force damage may result in errors in the measured distal pressure $P_d$.

Accordingly, there is a need for systems, and methods for manufacturing such systems, to reduce the occurrence of contact and bending force damage to a pressure sensor of a distal shaft of a FFR catheter.

BRIEF SUMMARY OF THE INVENTION

Embodiments hereof relate to a distal shaft for measuring a pressure distal of a stenosis including a housing, a pressure sensor, a cover, a tip, and an aperture. The pressure sensor is mounted in the housing. The cover is coupled to the housing and covers the pressure sensor. The tip is coupled to the distal end of the housing. The aperture is disposed though the tip and/or cover. The aperture is configured to allow blood flow to the pressure sensor.

Embodiments hereof also relate to a system for calculating a Fractional Flow Reserve of a stenosis in a blood vessel including a catheter, a proximal pressure-sensing device, and a processing device. The catheter includes a distal shaft with a housing including a distal pressure sensor mounted therein, a separate cover coupled to the housing, and a tip including an aperture. The aperture is configured to provide blood flow to the pressure sensor. The distal shaft is configured for placement within a blood vessel such that blood distal of the stenosis flows through the aperture into the housing and is in contact with the distal pressure sensor. The distal pressure sensor measures a distal blood pressure distal of the stenosis. The proximal pressure-sensing device is configured to measure a proximal blood pressure proximal of the stenosis. The processing device is in communication with the distal pressure sensor and the proximal pressure-sensing device. The processing device is configured to calculate a Fractional Flow Reserve based on the distal blood pressure relative to the proximal blood pressure.

Embodiments hereof also relate to a method of manufacturing a distal shaft of an FFR catheter for measuring a distal pressure measurement on a distal side of a stenosis. A cover is positioned at a housing of a distal shaft. The housing includes a pressure sensor mounted therein. The cover is coupled to the housing of the distal shaft to cover the pressure sensor. An aperture is provided through the cover and/or a portion of the distal shaft. The aperture is configured to enable blood flow into the housing and into contact with the pressure sensor.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter or delivery system are with respect to a position or direction relative to the treating clinician. Thus, "distal" and "distally" refer to positions distant from, or in a direction away from the treating clinician, and the terms "proximal" and "proximally" refer to positions near, or in a direction toward the clinician. The terms "distal" and "proximal" used in the following description to refer to a vessel or a stenosis are used with reference to the direction of blood flow. Thus, "distal" and "distally" refer to positions in a downstream direction with respect to the direction of blood flow, and the terms "proximal" and "proximally" refer to positions in an upstream direction with respect to the direction of blood flow.

The following detailed description is merely exemplary in nature and is not intended to limit the invention or the application and uses of the invention. Although the description of the invention is in the context of treatment of blood vessels such as the coronary arteries, the invention may also be used in any other body passageways where it is deemed useful such as but not limited to peripheral arteries, carotid arteries, renal arteries, and/or venous applications. Furthermore, there is no intention to be bound by any expressed or implied theory presented in the preceding technical field, background, brief summary or the following detailed description.

Figure 1:
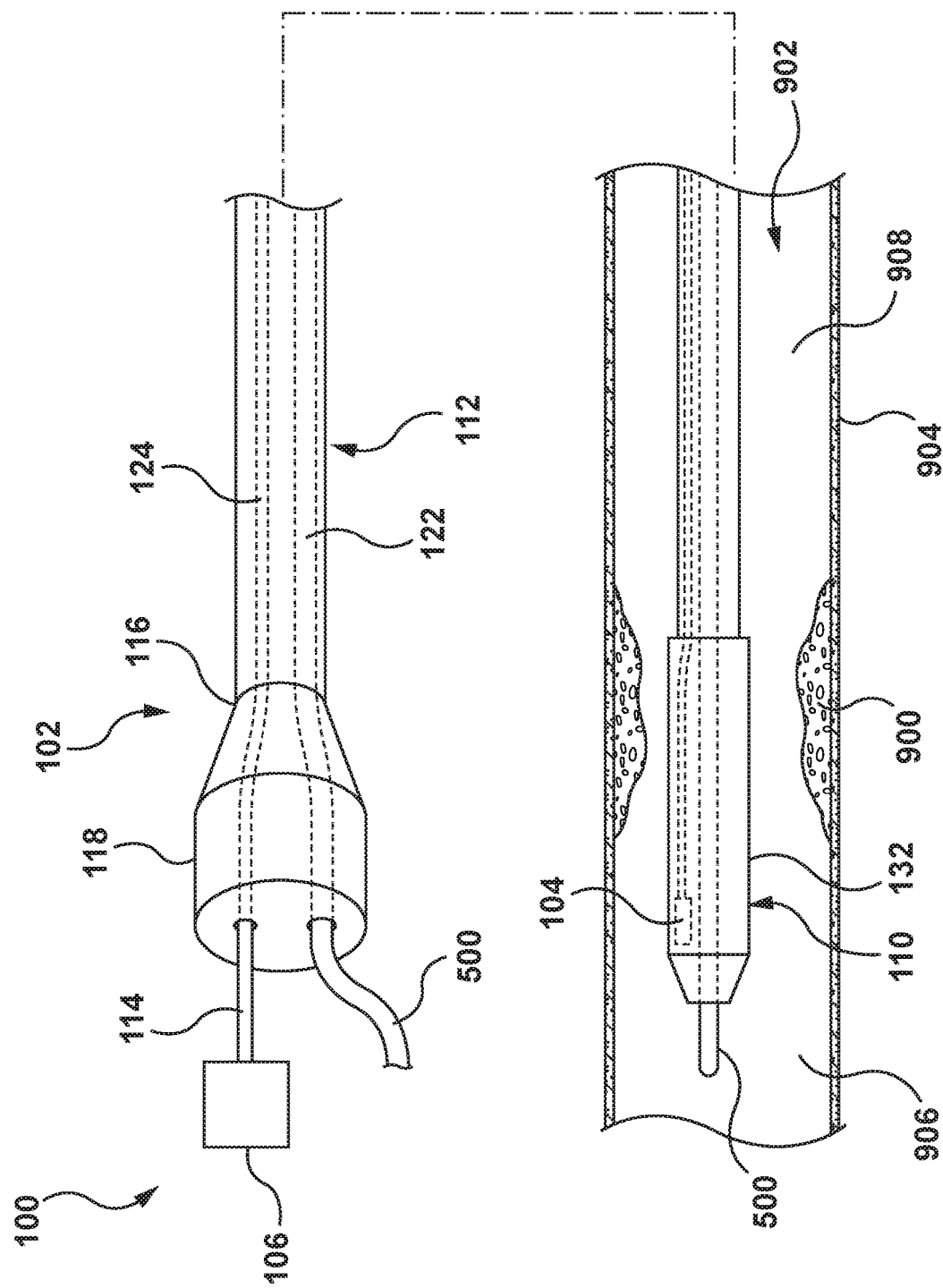
FIG. 1 is a partial side and perspective illustration of a catheter for calculating a Fractional Flow Reserve (FFR) in accordance with an embodiment hereof.

FIG. 1 is a schematic partial side and partial perspective illustration of a system 100 for calculating a Fractional Flow Reserve (FFR) according to an embodiment hereof. The system 100 includes an FFR catheter or micro-catheter 102, a proximal pressure-sensing device (not shown), and a processing device 106. The catheter 102 is configured to be disposed with a proximal portion thereof extending outside of a patient and a distal portion thereof positioned in situ within a lumen 902 of a vessel 904 having a stenosis 900. In an embodiment, the vessel 904 is a blood vessel such as but not limited to a coronary artery. The stenosis 900 is generally representative of any blockage or other structural arrangement that results in a restriction to the flow of fluid through a lumen 902 of the vessel 904. The stenosis 900 may be a result of plaque buildup, including without limitation plaque components such as fibrous, fibro-lipidic (fibro fatty), necrotic core, calcified (dense calcium), blood, fresh thrombus, and mature thrombus. Generally, the composition of stenosis 900 will depend on the type of vessel being evaluated. In that regard, it is understood that embodiments hereof are applicable to various types of blockages or other narrowing of a vessel that results in decreased fluid flow.

Figure 2:
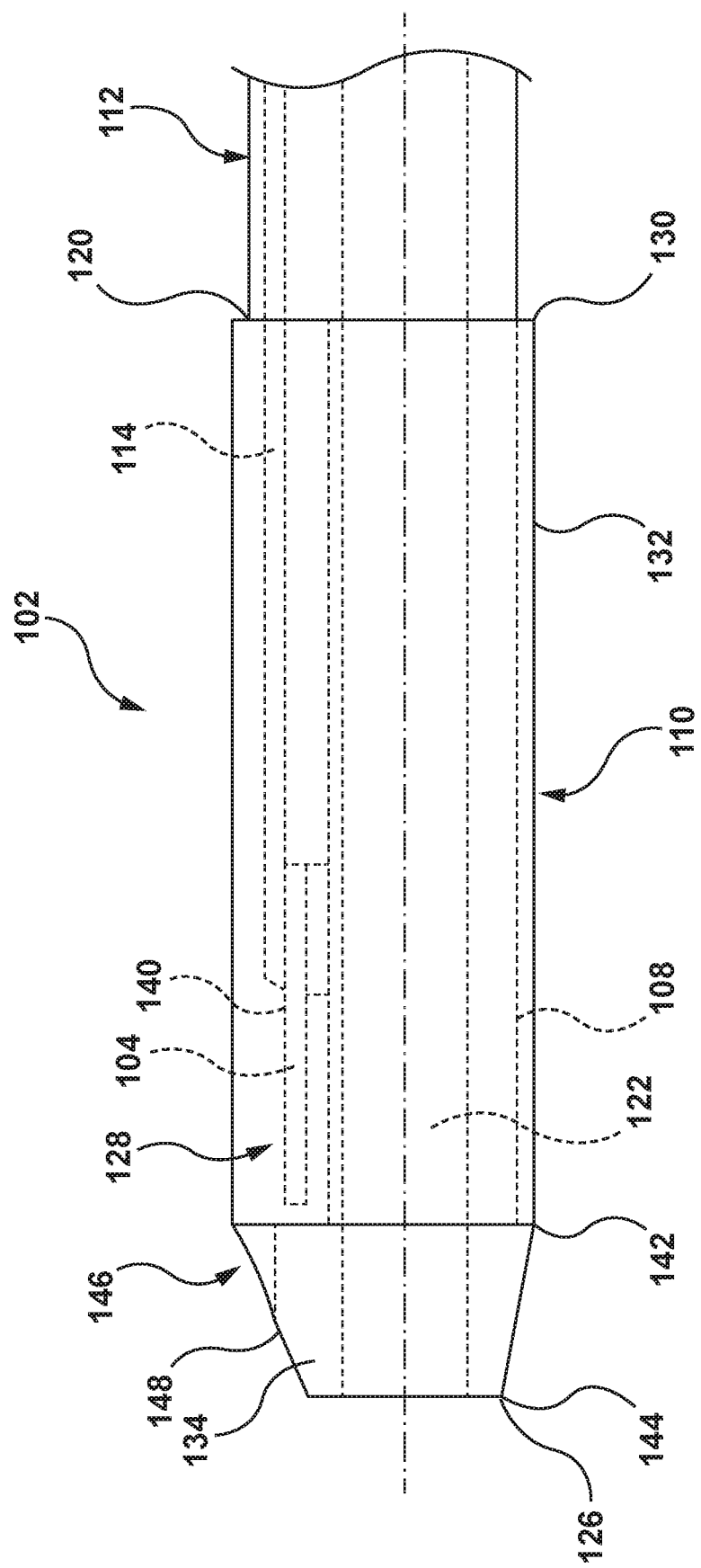
FIG. 2 is a side illustration of a distal shaft of the catheter of FIG. 1.

The catheter 102 includes a proximal shaft 112 and a distal shaft 110. A pressure sensor 104, shown in FIG. 1 and in greater detail in FIG. 2, is disposed in a housing 108 of the distal shaft 110. The pressure sensor 104 is coupled to the housing 108 and covered by a cover 132, as described in greater detail below. The cover 132 is configured to protect the pressure sensor 104 during handling and use of the catheter 102. The cover 132 is a separate piece attached to the housing 108 during manufacture to simplify manufacturing of the distal shaft 110 with the pressure sensor 104 disposed therein. As used herein, the term "separate" when used to describe that the cover 132 is a "separate" piece attached to the housing 108 during manufacture, it is meant that the cover 132 is not formed as part of the housing 108. Instead, the two pieces are separate and then are attached as described below during manufacture. Thus, for example, and not by way of limitation, a housing that is formed with a portion covering a pressure sensor would not be a "separate" cover. Similarly, a "cover" that is co-formed with a "housing", such as by molding, is not considered a separate cover attached to the housing.

In the embodiment shown in FIG. 1, catheter 102 includes a guidewire lumen 122 extending through the proximal shaft 112 and the distal shaft 110. The guidewire lumen is configured to receive a guidewire 500. However, instead of the over-the-wire configuration shown in FIG. 1, catheter 102 may have a rapid exchange configuration wherein the guidewire lumen 122 extends through the distal shaft 110 and a portion of the proximal shaft 112, and the guidewire 500 exits through a rapid exchange port (not shown) in a distal portion of the proximal shaft 112, as would be understood by those skilled in the art. Catheter 102 also includes a sensor wire lumen 124 extending through the proximal shaft 112 and the distal shaft 110 to the pressure sensor 104. The proximal shaft 112 includes a proximal end 116 coupled to a hub or luer 118 and a distal end 120 coupled to the distal shaft 110.

In an embodiment, the distal shaft 110 of the catheter 102 includes a proximal end 130 coupled to a distal end 120 of the proximal shaft 112, and a distal end 126, as shown in FIG. 2. A distal portion of the guidewire lumen 122 extends through the distal shaft 110. The distal shaft 110 includes the housing 108, the pressure sensor 104, the cover 132, a distal tip 134, and an aperture 146 through the distal tip 134, as described in more detail below. The distal shaft 110 is configured such that the pressure sensor 104 and the tip 134 are disposed on the distal side 906 of the stenosis 900 such that the pressure sensor 104 can measure a distal pressure $P_d$ distal of the stenosis 900, as shown in FIG. 1.

Figure 3:
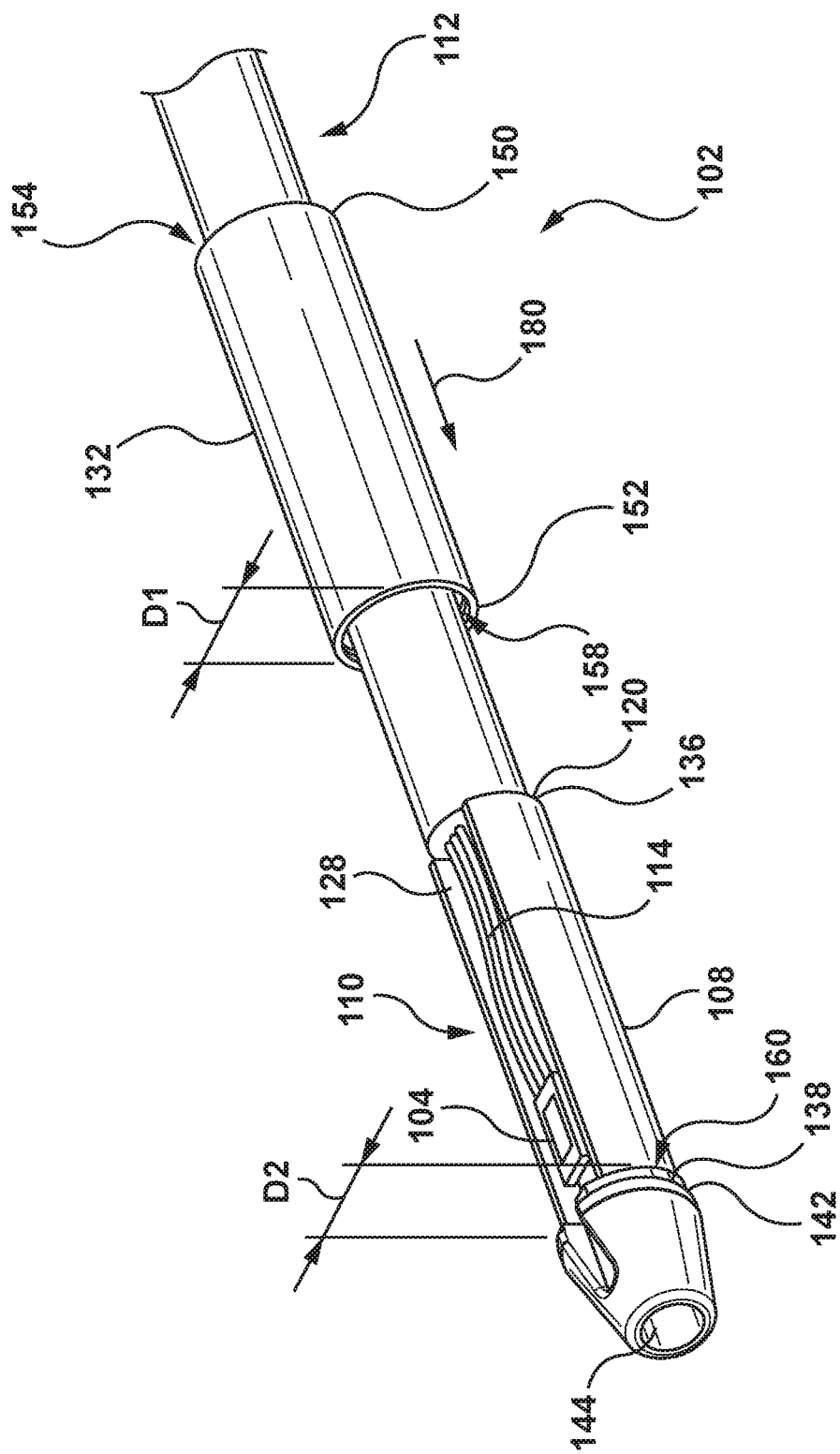
FIG. 3 is a perspective illustration of a distal shaft of the catheter of FIG. 1 according to an embodiment hereof, with a cover with a snap-fit coupling mechanism in a first configuration.
Figure 5:
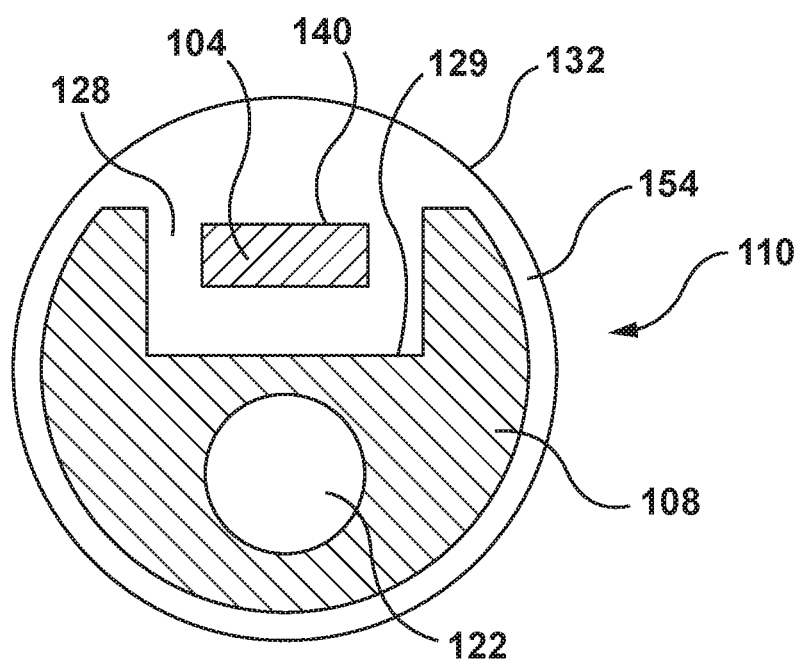
FIG. 5 is a cross-sectional illustration of the distal shaft of FIG. 3, taken along line 5-5 of FIG. 4.
Figure 5A:
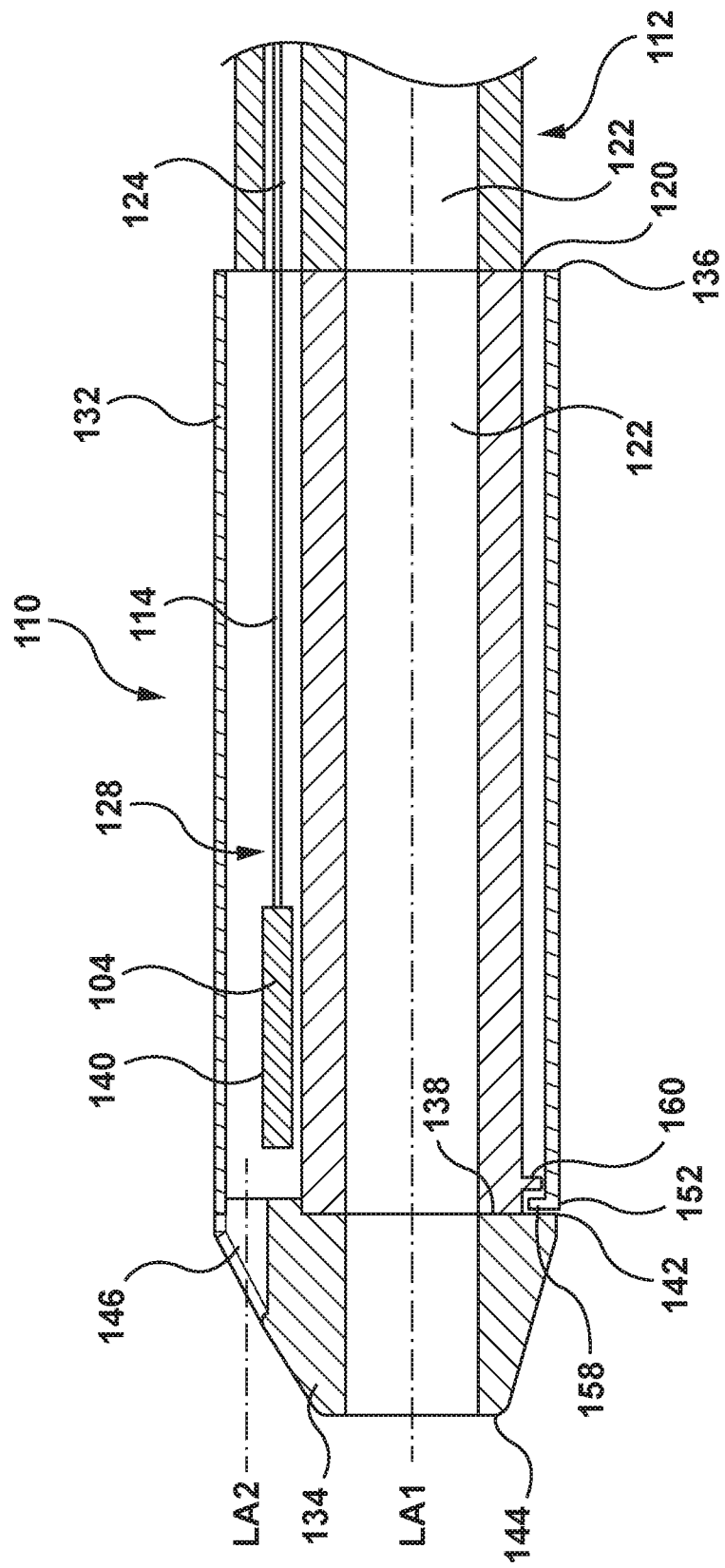
FIG. 5A is a longitudinal cross-sectional illustration of the distal shaft of FIG. 3 taken along line 5A-5A of FIG. 3.

In an embodiment, the housing 108 of the distal shaft 110 is of a generally tubular shape having a proximal end 136 coupled to the distal end 120 of the proximal shaft 112 and a distal end 138 coupled to the distal tip 134, as shown in FIGS. 3 and 5A. The housing 108 defines an open seat 128, extending from an outer surface of the housing 108 inward. In particular, referring to FIG. 5, the open seat 128 may be defined by groove or depression 129 in the housing 108. The open seat 128 is configured to receive the pressure sensor 104 therein. The open seat 128 is further configured to receive a fluid therein from the aperture 146, as described in greater detail below. The housing 108 may be formed of polymeric materials, non-exhaustive examples of which include polyethylene, polyether block amide (PEBA), polycarbonate, acrylonitrile butadiene styrene (ABS), polyether ether ketone (PEEK), polyamide and/or combinations thereof, either blended or co-extruded. The housing 108 may be coupled to the distal end 120 of the proximal shaft 112 and a proximal end 142 of the tip 134 by methods such as, but not limited to adhesives, fusing, welding, or any other method suitable for the purposes described herein. Alternatively, the housing 108 may be formed as an integral component of the proximal shaft 112 and the tip 134. The open seat 128 is shown as a generally rectangular cuboid. However, this is not meant to be limiting and open seat 128 may be of any shape to house the pressure sensor 104 and provide sufficient space for fluid entering therein for the pressure sensor 104 to measure a pressure of the fluid.

The pressure sensor 104 includes a pressure-sensing surface 140, as shown in FIGS. 2, 5, and 5A. The pressure sensor 104 may be a piezo-resistive pressure sensor, a piezo-electric pressure sensor, a capacitive pressure sensor, an electromagnetic pressure sensor, an optical pressure sensor, and/or combinations thereof suitable for the purpose described herein. While the pressure sensor 104 is shown in FIG. 2 configured with the pressure-sensing surface 140 facing radially outward, the pressure-sensing surface 140 may face in other directions such that pressure-sensing surface 140 measures distal pressure $P_d$ of a fluid outside the distal shaft 110 that has entered the open seat 128 through the aperture 146. The pressure sensor 104 is further configured to communicate a measured distal pressure $P_d$ with the processing device 106 through the pressure sensor wire(s) 114, as described in U.S. Patent Application Publication No. 2015/0305633 A1 to McCaffrey et al., incorporated by reference herein in its entirety. The pressure sensor 104 is disposed within and coupled to the open seat 128 of the housing 108. The open seat 128 and/or the pressure sensor 104 may include tabs, arms, slots, or other devices suitable to enhance coupling of the pressure sensor 104 in the open seat 128. The pressure sensor 104 may be coupled to the open seat 128, for example, and not by way of limitation, by adhesives, fusing, welding, or any other method suitable for the purposes of the present disclosure. The pressure sensor 104 is further coupled to the pressure sensor wire(s) 114. The pressure sensor 104 may be coupled to pressure sensor wire(s) 114 for example, and not by way of limitation, by soldering, fusing, welding, for any other method suitable for the purposes of the present disclosure.

In an embodiment, the tip 134 is of a generally frusto-conical shape. The tip 134 includes the proximal end 142 coupled to the distal end 138 of the housing 108, and a distal end 144, as shown in FIGS. 3 and 5A. The tip 134 may be formed of polymeric materials, non-exhaustive examples of which include polyethylene, polyether block amide (PEBA), polycarbonate, acrylonitrile butadiene styrene (ABS), polyether ether ketone (PEEK), polyamide and/or combinations thereof, or other materials suitable for the purposes described herein. Alternatively, the tip 134 may be formed as an integral component of the housing 108 of the distal shaft 110.

Figure 2A:
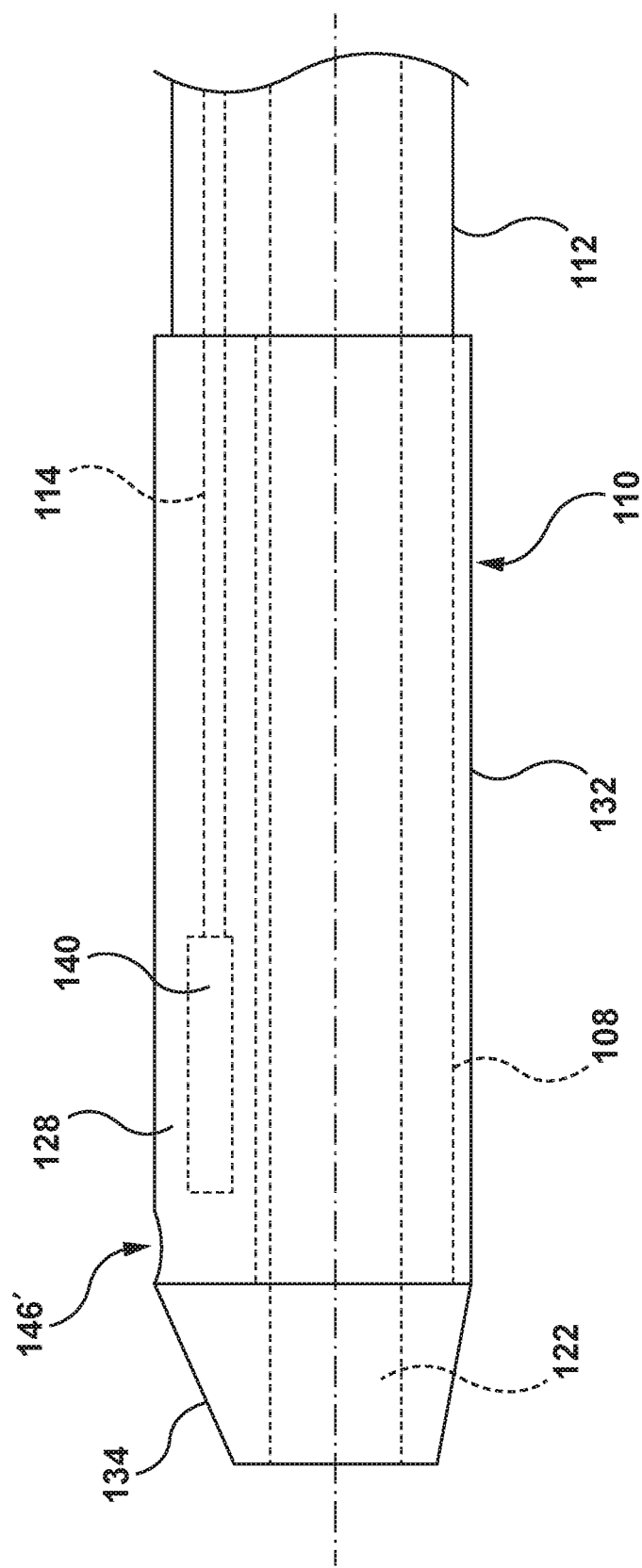
FIG. 2A is a side illustrated of a distal shaft with an aperture in a different location.

In an embodiment, the distal shaft 110 further includes the aperture 146 disposed through the tip 134 and in fluid communication with the open seat 128. The aperture 146 is generally aligned with the open seat 128. The aperture 146 is an opening extending from an outer surface 148 of the tip 134, through tip 134, and extends into the open seat 128 of the housing 108. The aperture 146 is configured to receive fluid therethrough such that the fluid outside the distal tip 134 may flow through the aperture 146 and into the open seat 128 of the housing 108. The fluid flows through the aperture 146 and into the open seat 128 such that the fluid is in contact with the pressure-sensing surface 140 of the pressure sensor 104. In an embodiment, the aperture 146 is aligned generally parallel to a central longitudinal axis LA1 of the distal shaft 110 such that the aperture 146 provides axial fluid flow to the open seat 128 and the pressure sensor 104 disposed therein. FIG. 5A shows an aperture central axis LA2 parallel to the central longitudinal axis LA1 of the distal shaft 110. The aperture 146 is sized such that a sufficient amount of blood flows into the open seat 128 of the housing 108 but tissue is prevented from entering the open seat 128 during advancement of the distal shaft 110 through a vasculature. In an embodiment, the aperture 146 is in the range of 100 to 500 microns. The aperture 146 may be formed as an integral component of the distal tip 134 or may be formed by removing material from the distal tip 134 by any suitable method such as, but not limited to cutting, machining, drilling, laser cutting, laser ablation, or other methods suitable for the purposes described herein. The aperture 146 is shown as generally tubular, but this is not meant to limit the design, and other shapes may be utilized. Moreover, while the aperture 146 is shown as a single aperture disposed through the tip 134, this is not meant to limit the design, and other configurations may be used. For example, and not by way of limitation, there may be multiple apertures 146. In another non-limiting example, the aperture 146 may be disposed through the cover 132, as shown in FIG. 2A.

Figure 4:
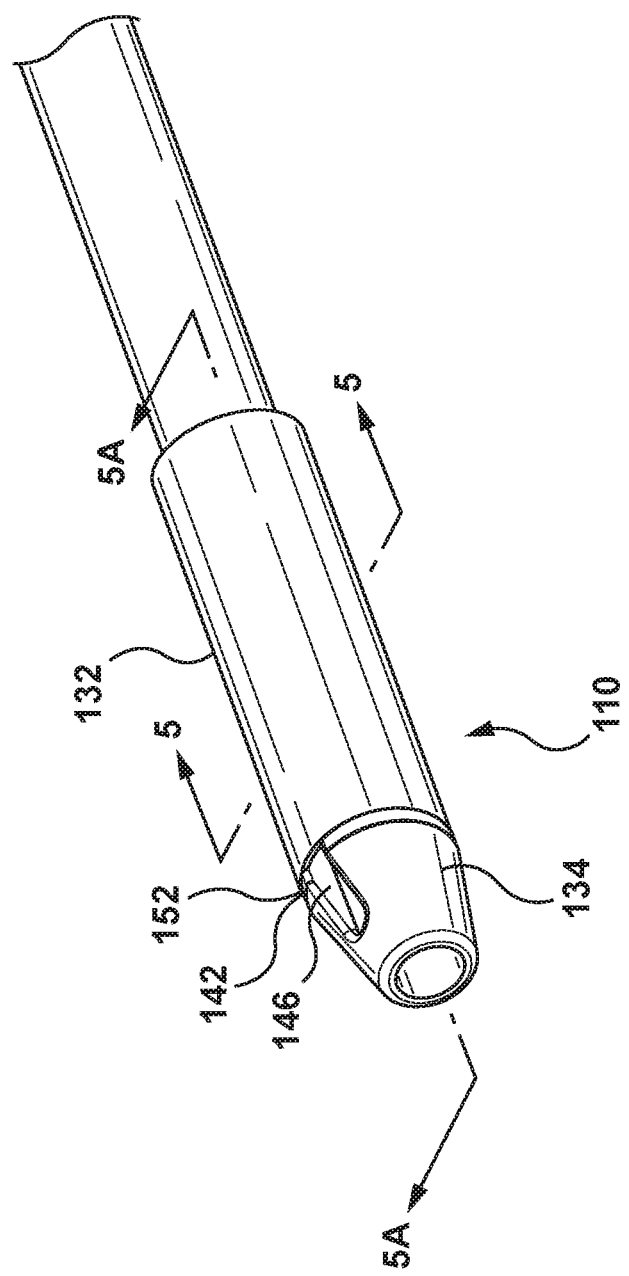
FIG. 4 is a perspective illustration of the distal shaft of FIG. 3, with the cover in a second configuration.

In an embodiment, the cover 132 is of a generally tubular shape with a proximal end 150, a distal end 152, and a cover lumen 154 extending through the cover 132 between the proximal and distal ends 150, 152, as shown in FIGS. 3 and 5. The cover 132 may be disposed in a first configuration, as shown in FIG. 3, wherein the cover 132 is not coupled to the housing 108 and is disposed proximal to the housing 108. The first configuration is used during manufacture to simplify installation of the sensor 104 and connection of the sensor 104 to the sensor wire(s) 114. The cover 132 is moved during manufacturing to a second configuration, as shown in FIG. 4, wherein the cover 132 is coupled to the housing 108 such that the housing 108 is disposed within the cover lumen 154. As explained above, the cover 132 is configured to protect the pressure sensor 104 when the cover 132 is in the second configuration. More specifically, the cover 132 prevents contact damage to the pressure sensor 104 during handling, or contact with tissue during advancement of the catheter 102 through a vasculature of a patient. The cover 132 may be formed of a second material different than a first material of the housing 108 such that the cover 132 is more rigid than the housing 108. The increased rigidity of the cover 132 resists bending of the distal shaft 110, especially in areas adjacent to the cover 132, as the distal shaft 110 advances through the vasculature of the patient. Thus, the more rigid cover 132 protects the pressure sensor 104 from bending damage or bending stresses incurred during handling or advancement through the vasculature of the patient. The cover 132 is coupled to housing 108 by a coupling mechanism such as, but not limited to a friction-fit mechanism, a snap-fit mechanism, adhesives, or any other coupling mechanism suitable for the purposes described herein. The cover 132 may be formed of metals such as, but not limited to, stainless steel, gold, platinum, and/or iridium, and alloys thereof. In some embodiments, such as forming the cover 132 of gold, platinum, platinum-iridium alloys, and other radiopaque materials, the cover 132 may also act as a marker band. In other embodiments, the cover 132 may be formed of metal reinforced polymers, polycarbonate, acrylonitrile butadiene styrene (ABS), polymers (e.g. polyether ether ketone (PEEK)), reinforced polymers (e.g. carbon fiber), or other materials suitable for the purposes described herein.

FIGS. 3 and 5A show the cover 132 and the housing 108 with a snap-fit coupling mechanism according to an embodiment hereof. The snap-fit coupling mechanism includes a first annular ring 158 extending radially inward from an inside surface of the cover 132 and a corresponding second annular ring 160 extending radially outward from an outer surface of the housing 108. The inner diameter D1 of the first annular ring 158 of the cover 132 in the first configuration is smaller than the outer diameter D2 of the corresponding second annular ring 160 of the housing 108. When the cover 132 is moved distally in the direction of arrow 180 with sufficient force, the distal portion of the cover 132 deforms slightly radially outwardly for the first annular ring 158 of the cover 132 to move over the second annular ring 160 of the housing 108. Upon clearing the second annular ring 160, the cover 132 returns to its initial shape such that the first annular ring 158 is distal of the second annular ring 160, as shown in FIG. 5A. This locks the cover 132 in place. The annular rings 158, 160 may include angled faces such as to minimize the force required to move the cover 132 distally over the second annular ring 160 while preventing movement of the cover 132 in a proximal direction. Thus, the cover 132 has been transitioned from the first configuration to the second configuration. When in the second configuration, the distal end 152 of the cover 132 is adjacent to the proximal end 142 of the tip 134, as shown in FIG. 5A. Moreover, when the cover 132 is in the second configuration, as shown in FIGS. 4 and 5A, the cover 132 encircles an outer surface of the housing 108 and the pressure sensor 104. The annular rings 158, 160 are shown as being disposed at distal portions of the cover 132 and housing 108, respectively. However, this is not meant to be limiting and annular rings may instead be disposed anywhere along the length of the cover 132 and the housing 108. Further, the annular rings 158, 160 do not need to extend around the entire circumference of the cover 132 and the housing 108. Instead, the annular rings may be several protrusions or ring segments extending from the inner surface of the cover 132 and the outer surface of the housing 108, with circumferential gaps between the ring segments. Further, adhesives or other coupled mechanisms may be added to the snap-fit coupling described. Still further, other snap-fit mechanisms suitable for the purposes described herein may be utilized.

Figure 6:
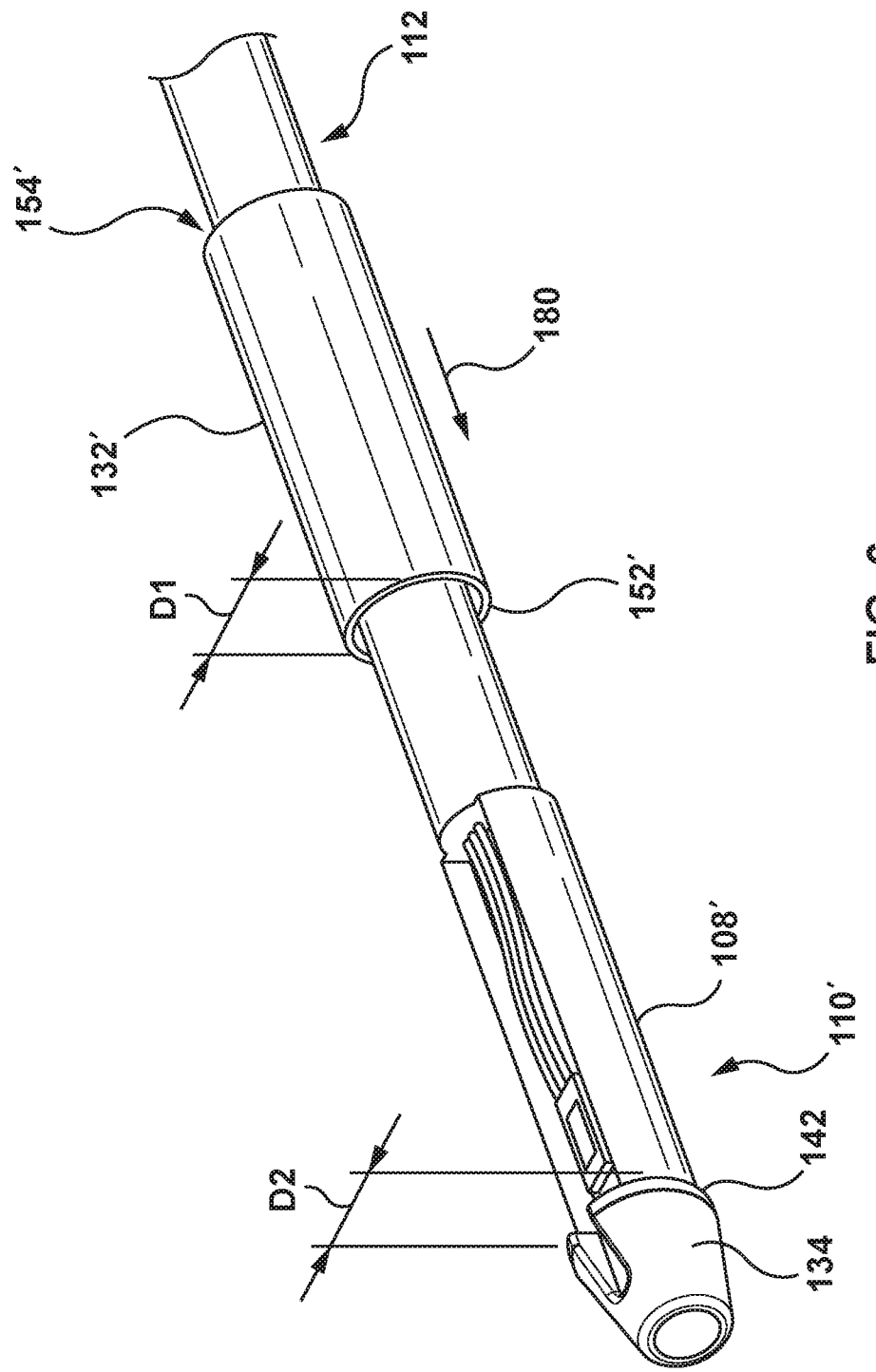
FIG. 6 is a perspective illustration of the distal shaft of the catheter of FIG. 1, with the cover with a friction-fit coupling mechanism in the first configuration.

FIG. 6 shows another embodiment of cover 132' that may be used with the catheter 102 of FIG. 1. The cover 132' is similar to the cover 132 described previously, except that the cover 132' utilizes a friction-fit coupling mechanism for coupling the cover 132' to a housing 108'. Other than the cover 132' and the housing 108', the remaining features of the catheter 102 remain as described above, and therefore will not be described here. In the embodiment shown, a distal portion of the cover 132' has a first inner diameter D1 when the cover 132' is in the first configuration. A corresponding distal portion of the housing 108' has a second outer diameter D2, wherein the first diameter D1 is smaller than the second diameter D2. Thus, with cover 132' in the first configuration disposed over the distal portion of the proximal shaft 112, application of a sufficient force distally (in the direction of arrow 180) to the cover 132' will slide or translate the cover 132' distally over the housing 108'. More specifically, with a sufficient force applied thereto, the cover 132' will radially expand to match the larger diameter outer surface of the housing 108'. The cover 132' will attempt to radially collapse to its original shape, thereby coupling the cover 132' to the housing 108' via a friction fit. While the friction fit coupling is described at the corresponding distal ends of the cover 132' and the housing 108', this is not meant to be limiting. Thus, the friction fit may be at the respective proximal ends or over an entire length of the cover 132' and the housing 108' Further, an adhesive or other coupling mechanism may be added to the friction fit coupling to further secure the cover 132' to the housing 108'.

Referring to FIGS. 7-11, another embodiment of an FFR catheter or micro-catheter 302 is shown. Catheter 302 includes a proximal shaft 312, a distal shaft 310, and a pressure sensor 304. Further, the distal shaft 310 includes a housing including an open seat 328, a distal tip 334, and an aperture 346. These components are similar to the components described above with respect to catheter 102. Therefore, details and alternatives of these similar components will not be repeated. The embodiment of FIGS. 7-11 differs from the embodiments of FIGS. 1-6 in that the cover 332 is of a generally partial cylindrical shape. Further, the connection between the cover 332 and the housing 308 is different than the connection between the cover 132 and the housing 108.

Figure 7:
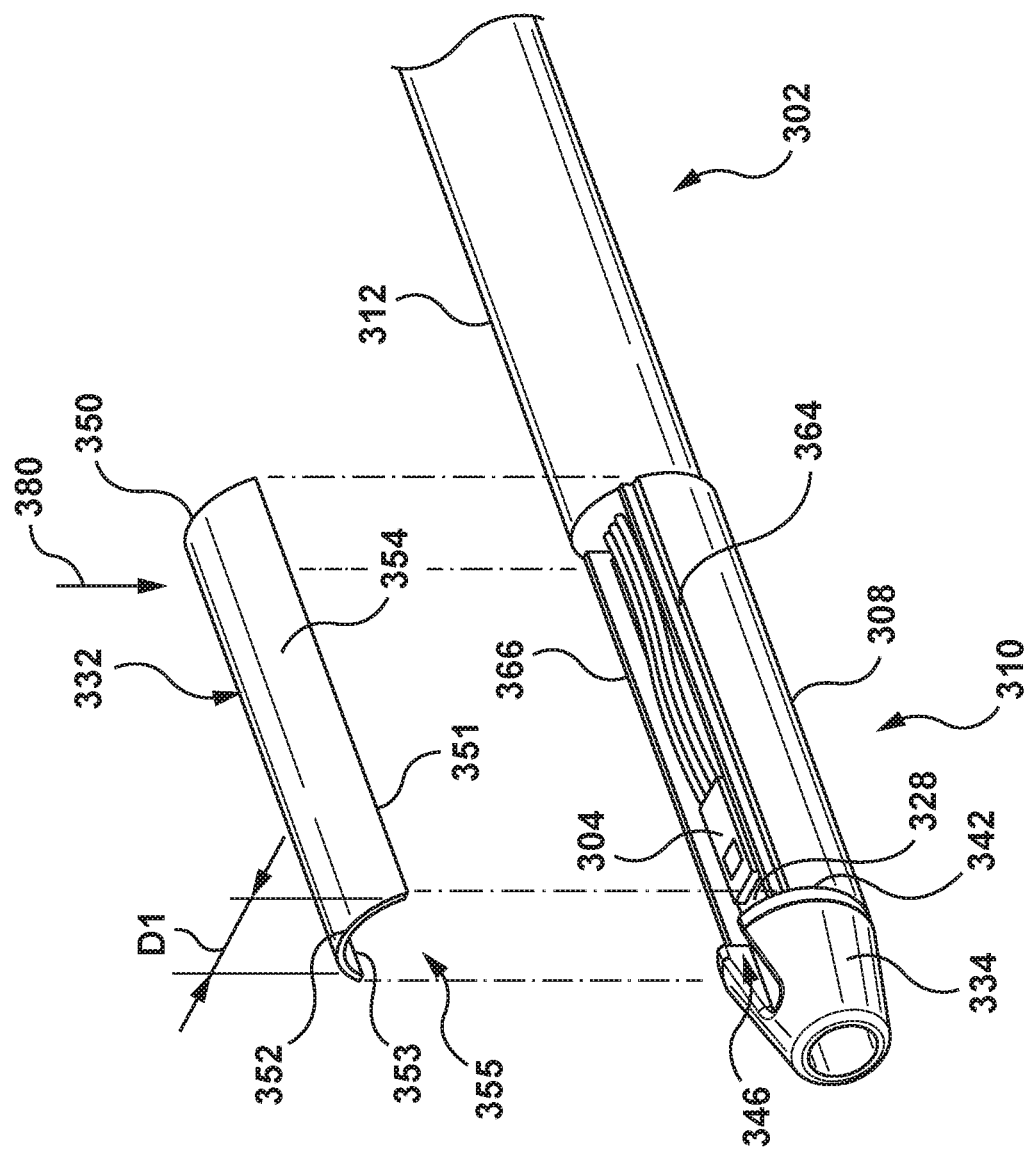
FIG. 7 is a perspective illustration of another embodiment of a catheter with another embodiment of a cover with a friction-fit coupling mechanism in a first configuration.
Figure 8:
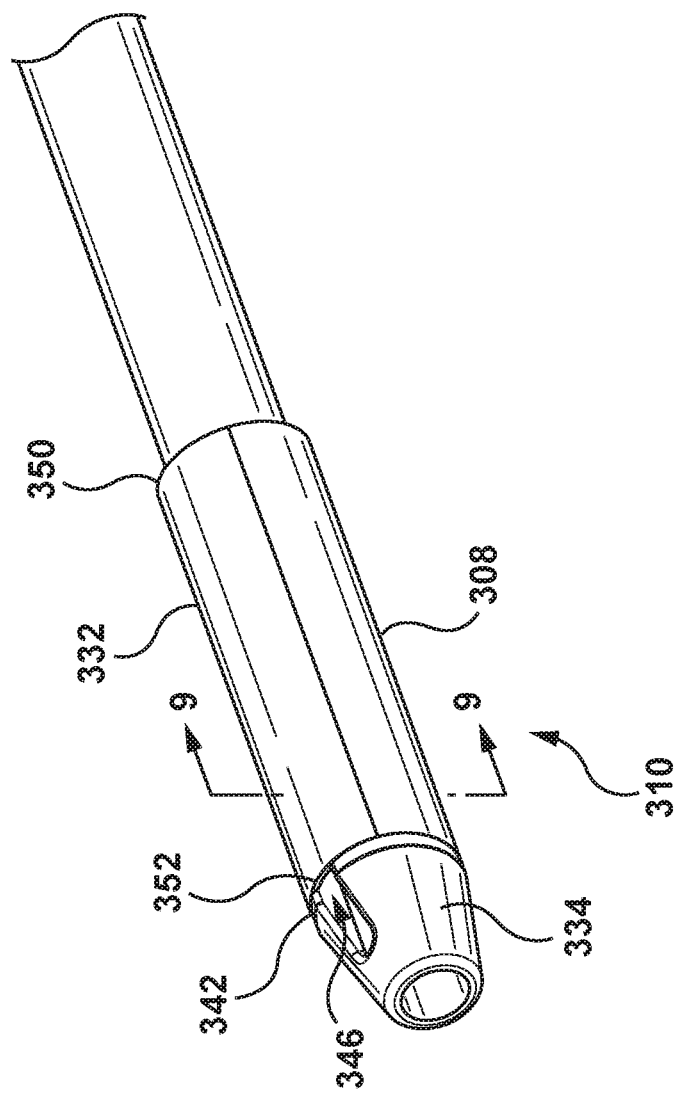
FIG. 8 is a perspective illustration of the distal shaft of FIG. 7, with the cover in a second configuration.
Figure 9:
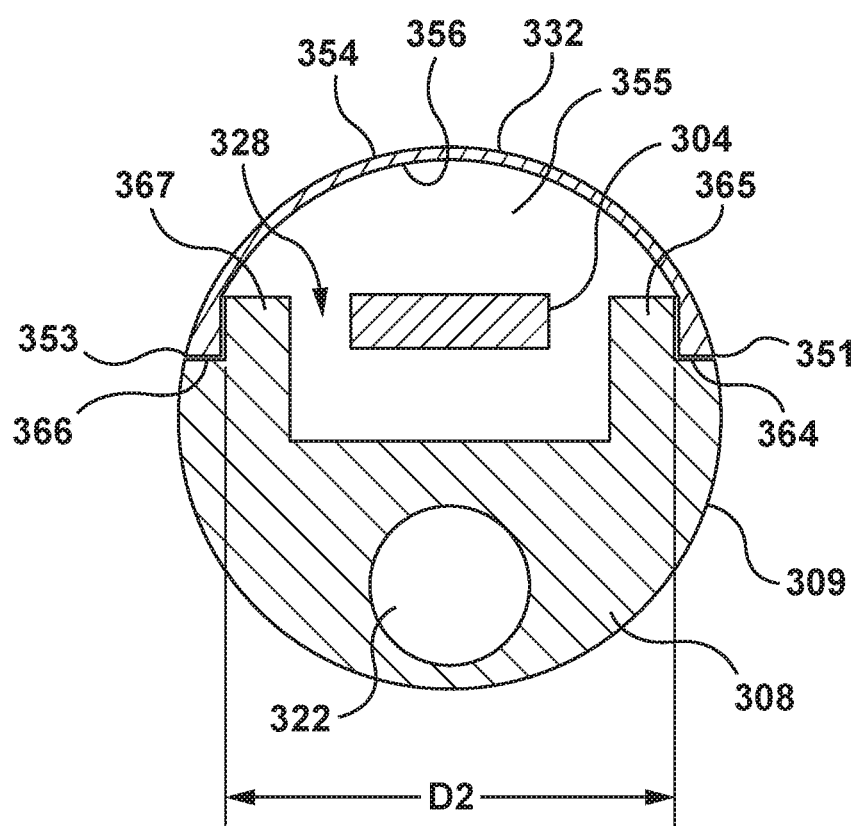
FIG. 9 is a cross-sectional illustration of the distal shaft of FIG. 8, taken along line 9-9 of FIG. 8.

In an embodiment, the cover 332 is of a generally partial cylindrical shape. The cover 332 includes a proximal end 350, a distal end 352, a first circumferential edge 351, and a second circumferential edge 353, as shown in FIGS. 7 and 9. An outer surface 354 and an inner surface 356 of the cover 332 are defined between the proximal end 350, the distal end 352, the first circumferential edge 351, and the second circumferential edge 353, as shown in FIG. 7. The outer and inner surfaces 354, 356 define a partial cylinder with an open portion 355 adjacent the inner surface 356, opposite the outer surface 354. The cover 332 includes a first configuration wherein the cover 332 is not coupled to the housing 308, as shown in FIG. 7, and a second configuration wherein the cover 332 is coupled to the housing 308, as shown in FIGS. 8-9. In the second configuration, the open portion 355 of the cover 332 is aligned with and covers the open seat 328 of the housing 308, as shown in FIGS. 8-9. With the cover 332 in the first configuration and positioned over the housing 308 such that the open portion 355 of the cover 332 is aligned with the open space 328 of the housing 308, the cover 332 may transition to the second configuration by moving the cover 332 towards the central longitudinal axis LA1 of the housing 308, as indicated by arrow 380 in FIG. 7. Stated another way, with the cover 332 in the first configuration and disposed over the corresponding open space 328 of the housing 308, the cover 332 may be pressed down onto the housing 308 to transition to the second configuration, as shown in FIGS. 8-9.

The cover 332 is configured to protect the pressure sensor 304 when the cover 332 is in the second configuration, i.e., when the cover 332 is coupled to the housing 108. More specifically, and as described previously, the cover 332 prevents contact damage to the pressure sensor 304 during handling, or contact with tissue during advancement of the catheter 302 through the vasculature of a patient. The cover 332 may be formed of a second material different than a first material of the housing 308 such that the cover 332 is more rigid than the distal housing 308. The increased rigidity of the cover 332 resists bending of the distal shaft 310 as the distal shaft 310 advances through the vasculature of the patient. Thus, the more rigid cover 332 protects the pressure sensor 304 from bending damage or bending stresses incurred during handling or advancement through the vasculature of the patient. The cover 332 is coupled to the housing 308 by a coupling mechanism such as, but not limited to a friction-fit mechanism, a snap-fit mechanism, adhesives, or any other coupling mechanism suitable for the purposes described herein. The cover 332 may be formed of metals such as, but not limited to, stainless steel, gold, platinum, and/or iridium, and alloys thereof. In some embodiments, such as forming the cover 332 of gold, platinum, platinum-iridium alloys, and other radiopaque materials, the cover 332 may also act as a marker band. In other embodiments, the cover 332 may be formed of metal reinforced polymers, polycarbonate, acrylonitrile butadiene styrene (ABS), polymers (e.g. polyether ether ketone (PEEK)), reinforced polymers (e.g. carbon fiber), or other materials suitable for the purposes described herein.

FIGS. 7-9 show the cover 332 with a friction-fit coupling mechanism according to an embodiment hereof. The cover 332 in the first configuration has a first distance D1 between the first circumferential edge 351 and the second circumferential edge 353, as shown in FIG. 7. The housing 308 includes a first shoulder 364 disposed in an outer surface 309 of the housing 308, adjacent to the open seat 328, and a second shoulder 366 disposed in the outer surface 309 of the housing 308, adjacent to the open seat 328, as shown in FIG. 7 and in greater detail in FIG. 9. The first and second shoulders 364, 366 extend inwardly from the outer surface 309 to first and second walls 365, 367, respectively, which extend generally perpendicular to first and second shoulders 364, 366, as shown in FIG. 9. The housing 308 has a second distance D2 between outer surfaces of the first wall 365 and the second wall 367, as shown in FIG. 9. The second distance D2 is greater than the first distance D1 between the first and second circumferential edges 351, 353 of the cover 332. Thus, when the cover 332 is in the second configuration coupled to the housing 308, the first circumferential edge 351 of the cover 332 is configured to align with and rest on the first shoulder 364 of the housing 308. Similarly, the second circumferential edge 353 of the cover 332 is configured to align with and rest on the second shoulder 366 of the housing 308. Because the first distance D1 between the first and second circumferential edges 351, 353 is smaller than the second distance D2 between the outer surfaces of the walls 365, 367, the cover 332 expands slightly radially outward for the first and second circumferential edges 351, 353 to clear the walls 365, 367 and sit on the first and second shoulders 364, 366. The cover 332 wants to return to its undeformed shape. Thus, the cover 332 squeezes radially inwardly on the respective outer surfaces of first and second walls 365, 367, thereby creating a friction fit between the cover 332 and the housing 308, as shown in FIG. 9. An adhesive or other coupling mechanism may be added to the friction fit to further secure the cover 332 to the housing 308.

Figure 10:
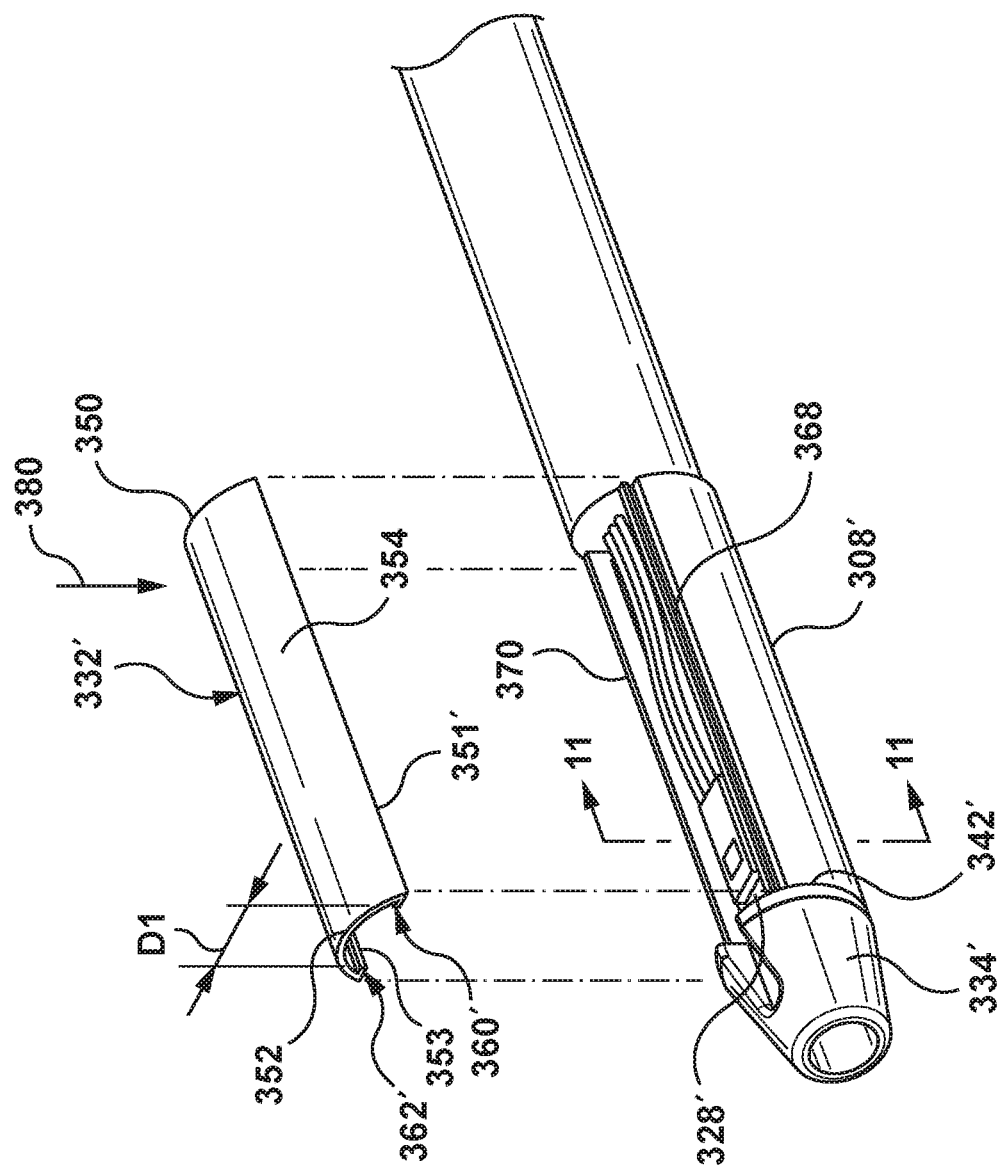
FIG. 10 is a perspective illustration of the distal shaft of FIG. 7, with the cover having a snap-fit coupling mechanism in the first configuration.
Figure 11A:
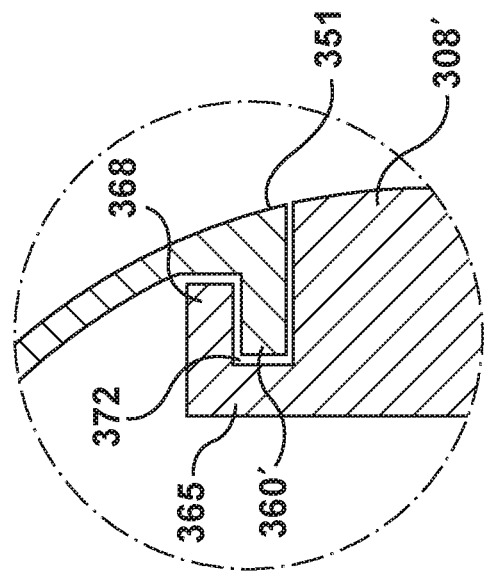
FIG. 11A is a detail view of area A of FIG. 11.
Figure 11:
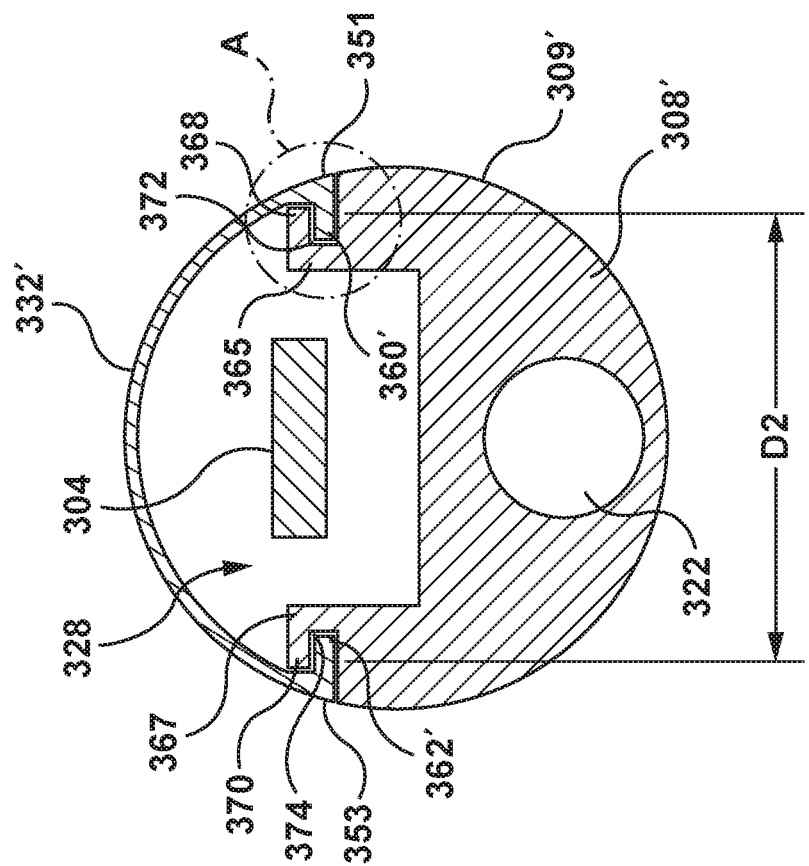
FIG. 11 is a cross-sectional illustration of the distal shaft of FIG. 10, taken along line 11-11 of FIG. 10 and with the cover in the second configuration.

FIGS. 10-11A show a cover 332' coupled to a housing 108' with a snap-fit connection. The cover 332' and the housing 308' are similar to the cover 332 and the housing 308 of FIGS. 7-9 except for the snap-fit connection.

Thus, the cover 332' includes a first protrusion or lip 360' extending generally radially inward from an inner surface of the cover 332', adjacent to the first circumferential edge 351'. A second protrusion or lip 362' extends generally radially inward from the inner surface of the cover 332', adjacent the second circumferential edge 353'. The first and second protrusions 360', 362' are generally opposite each other and extend towards each other. Further, the first and second protrusions 360', 362' extend longitudinally along the first and second circumferential edges 351, 353. With the cover 332' in the first configuration not coupled to the housing 308', the cover 332' has a first distance D1 between the first protrusion 360' and the second protrusion 362', as shown in FIG. 10.

The housing 308' of the distal shaft 310' includes a first lip 368 extending radially outwardly from the first wall 365' and a second lip 370 extending radially outwardly from the second wall 367', as shown in FIGS. 11 and 11A. Thus, a first channel 372 is formed between the first shoulder 364' and the first lip 368 and a second channel 374 is formed between the second shoulder 366' and the second lip 370. The first protrusion 360' fits within the first channel 372 of the housing 308' and the second protrusion 362' fits within the second channel 374 of the housing 308'. Further, a second distance D2 between outer surfaces of the first and second lips 368, 370 is larger than the first distance D1 between the first and second protrusions 360', 362' of the cover 332'. Thus, when the cover 332' is pushed towards the housing 308' the cover 332' expands radially outward for the first and second protrusions 360', 362' to clear the first and second lips 368, 370 of the housing 308'. The cover 332' continues to be pushed towards the housing 308' until the first and second protrusions 360', 362' clear the first and second lips 368, 370, respectively. The first and second protrusions 360', 362' then move radially inward into first and second channels 372, 374, respectively, as shown in FIGS. 11 and 11A. The first and second lips 368, 370 prevent the cover 332 from being lifted off of the housing 308'. An adhesive or other coupling mechanism may be added to the snap-fit connection of FIGS. 10-11A to further secure the cover 332' to the housing 308'.

Figure 12:
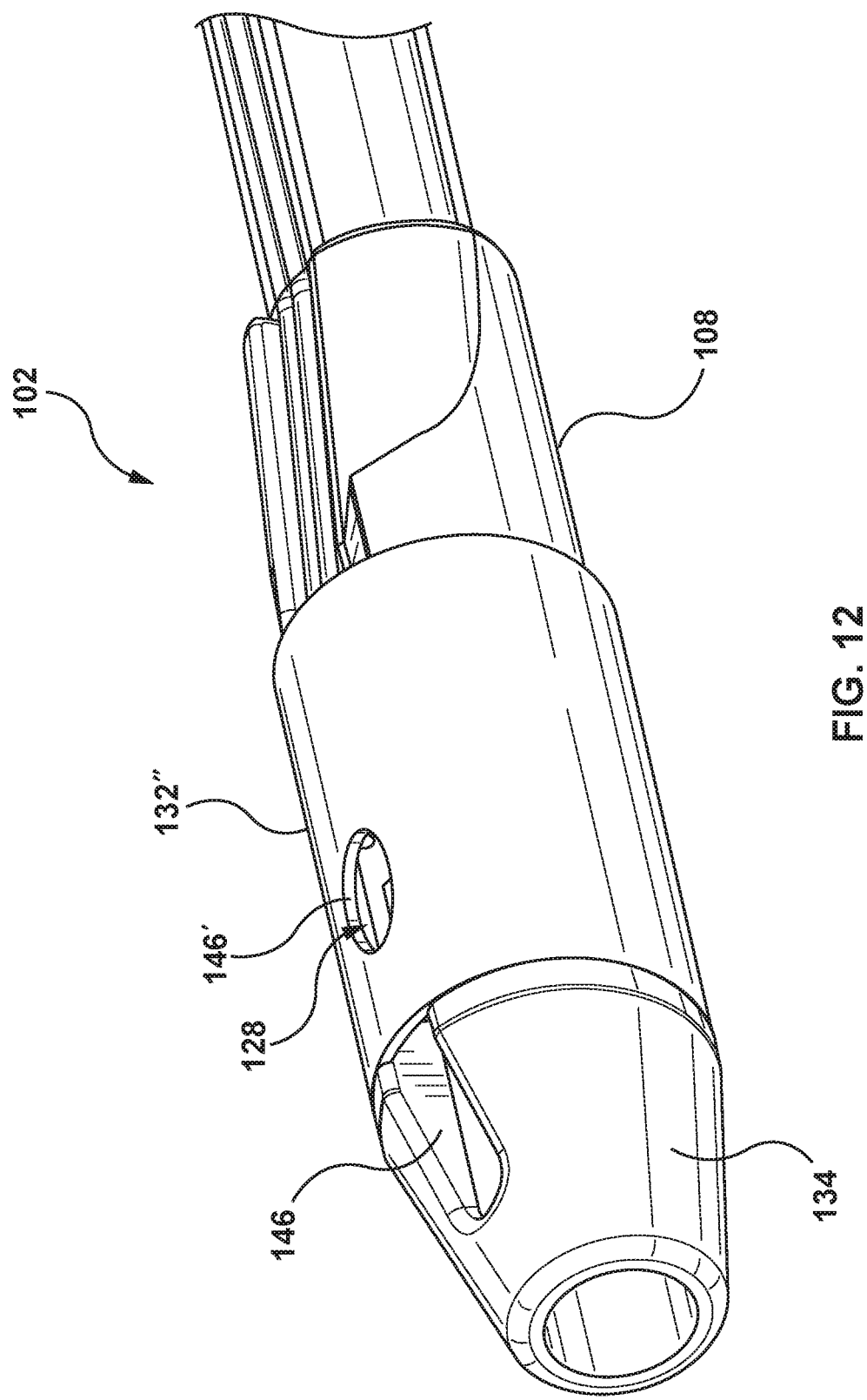
FIG. 12 is a perspective illustration of the distal shaft of another embodiment of a catheter with a first aperture disposed through the tip and a second aperture disposed through the cover.

As previously described, embodiments hereof may include more than one aperture disposed through the tip and/or the cover. Accordingly, another embodiment of a cover 132" useful with the catheter 102 of FIG. 1 is shown in FIG. 12. The catheter 102 includes a first aperture 146 disposed through the tip 134 and a second aperture 146' disposed through the cover 132". With the exception of the second aperture 146' of the cover 132", the remaining features of catheter 102 remain as described above, and therefore will not be repeated. In an embodiment, the second aperture 146' is disposed through the cover 132" and is in fluid communication with the open seat 128 of the housing 108. The second aperture 146' is an opening extending from an outer surface to an inner surface of the cover 132" and extends into the open seat 128 of the housing 108. The second aperture 146' is configured to receive fluid therethrough such that fluid outside the cover 132" may flow through the second aperture 146' and into the open seat 128 of the housing 108. Thus, fluid flows through both the first aperture 146 and the second aperture 146' into the open seat 128 such that the fluid is in contact with the pressure-sensing surface 140 of the pressure sensor 104. The first aperture 146 and the second aperture 146' are sized such that a sufficient amount of blood flows into the open seat 128 of the housing 108 but tissue is prevented from entering the open seat 128 during advancement of the distal shaft 110 through a vasculature. The second aperture 146' may be formed as an integral component of the cover 132" or may be formed by removing material from the cover 132" by any suitable method, non-limiting examples of which include cutting, machining, drilling, laser cutting; laser ablation, or other methods suitable for the purposes described herein. Although the second aperture 146' is shown as generally tubular with oval opening, this is not meant to be limiting, and other shapes may be utilized. Moreover, while the cover 132" is described herein with one (1) second aperture 146', it will be understood that the cover 132" may include more than one second aperture 146' and that the second aperture(s) 146' may be located at other locations of on the cover 132". Additionally, while described herein as an additional aperture in the generally tubular cover 132, it will be understood that an additional aperture or apertures may be disposed through embodiments of the partial cylindrical shaped cover 332 as well as in other embodiments of covers of the present disclosure.

Figure 13:
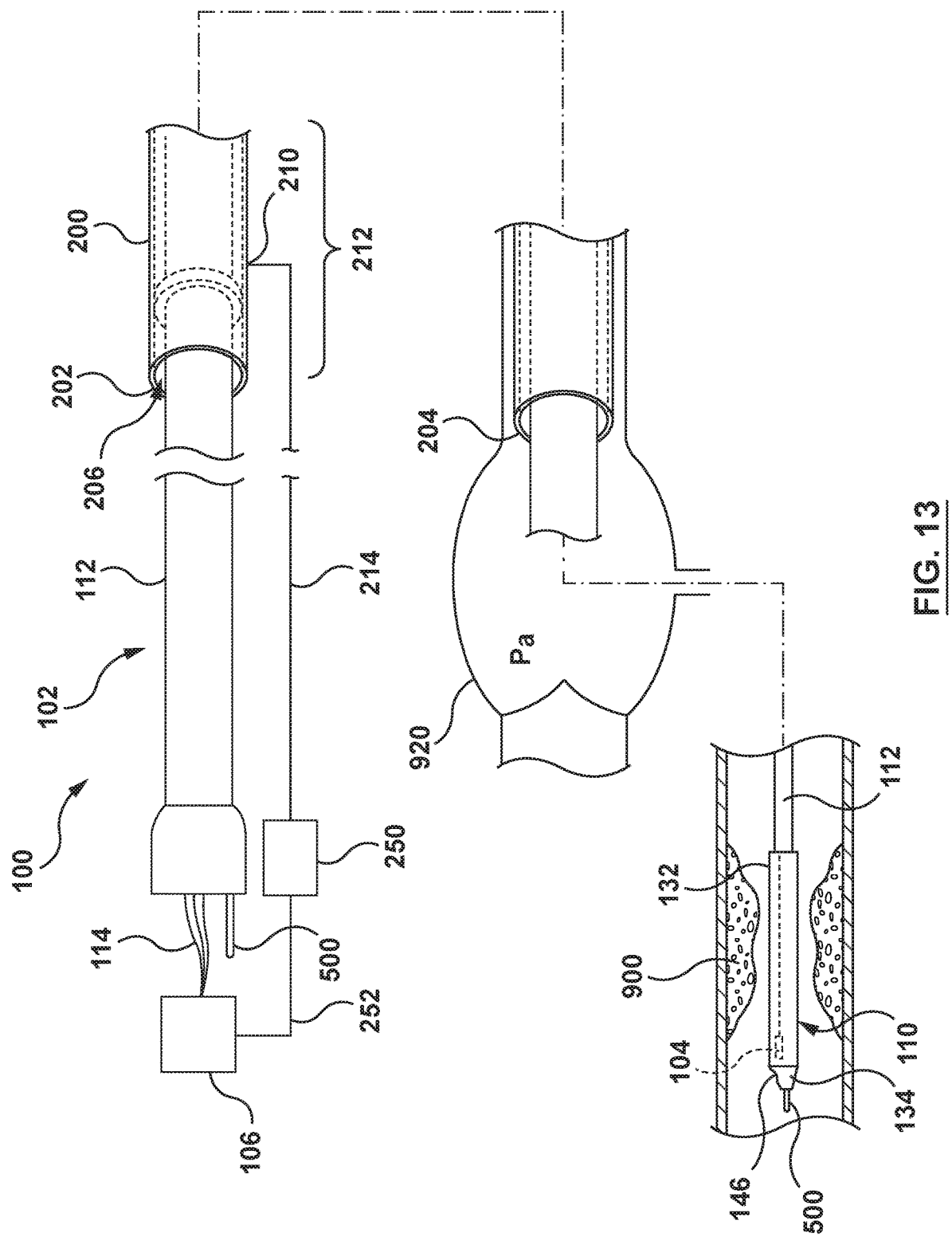
FIG. 13 is a schematic illustration of the system of FIG. 1 used to calculate a Fractional Flow Reserve.

With an understanding of the components above, it is now possible to describe their interaction as a system for measuring and calculating a Fractional Flow Reserve (FFR) according to an embodiment of the present disclosure. Referring to FIG. 13, the system 100 is shown disposed through a guide catheter 200, which is utilized as the proximal pressure-sensing device, as explained below. Referring to FIG. 13, the guide catheter 200 and the guidewire 500 are advanced through the vasculature to a desired site. The guidewire 500 may be back-loaded into the FFR catheter 102 (i.e., the proximal end of the guidewire 500 is loaded into the distal end of guidewire lumen 122 at the distal end 126 of the distal shaft 110). The FFR catheter 102 may then be advanced over the guidewire 500 and through a lumen 206 of the guide catheter 200 to the desired treatment site. In particular, with a distal end 204 of the guide catheter 200 disposed at a desired site proximal of the stenosis 900, such as in the sinus 920, the distal shaft 110 of the FFR catheter 102 is advanced through the lumen 206 and distal of the distal end 204 of the guide catheter 200. The FFR catheter 102 is advanced such that the distal shaft 110 is disposed through the stenosis 900 of the vessel 904. Blood flow from the aortic sinus 920 fills the lumen 206 and tubing 214 via a port 210 of a proximal portion 212 of the guide catheter 200. The blood pressure $P_a$ at the distal end 204 of the guide catheter 200 is measured by an external pressure transducer 250 via the fluid (blood) column extending through the lumen 206 and the tubing 214. Thus, the external pressure transducer 250 is configured to measure proximal, or aortic (AO) pressure $P_a$ at the distal end 204 of the guide catheter 200.

The external pressure transducer 250 is configured to communicate measured the proximal pressure $P_a$ to the processing device 106 via a pressure transducer wire 252, as shown in FIG. 13. While the pressure transducer 250 is shown in FIG. 13 as communicating the measured proximal pressure $P_a$ with the processing device 106 via the pressure transducer wire 252, this is not meant to limit the design and the pressure transducer 250 may communicate with the processing device 106 by any means suitable for the purposes described, including, but not limited to, electrical cables, optical cables, or wireless devices.

Simultaneously, blood on the distal side 906 of the stenosis 900 flows through the aperture 146 of the tip 134 and into the open seat 128 (FIG. 2) of the housing 108. The blood within the open seat 128 (FIG. 2) is in contact with the pressure-sensing surface 140 of the pressure sensor 104, coupled therein. The pressure within the open seat 128 is equal to the pressure on the distal side 906 of the stenosis 900. Thus, the distal pressure $P_d$ is sensed by the pressure sensor 104. The sensed distal pressure $P_d$ is communicated with the processing device 106. The processing device 106 calculates the Fractional Flow Reserve (FFR) based on the measured distal pressure $P_d$ divided by the measured proximal/aortic pressure $P_a$, or $FFR=P_d/P_a$.

Although the method described above refers to the FFR catheter 102, it applies equally to catheter 302 and to variations described above with respect to the catheters 102, 302.

Figure 14:
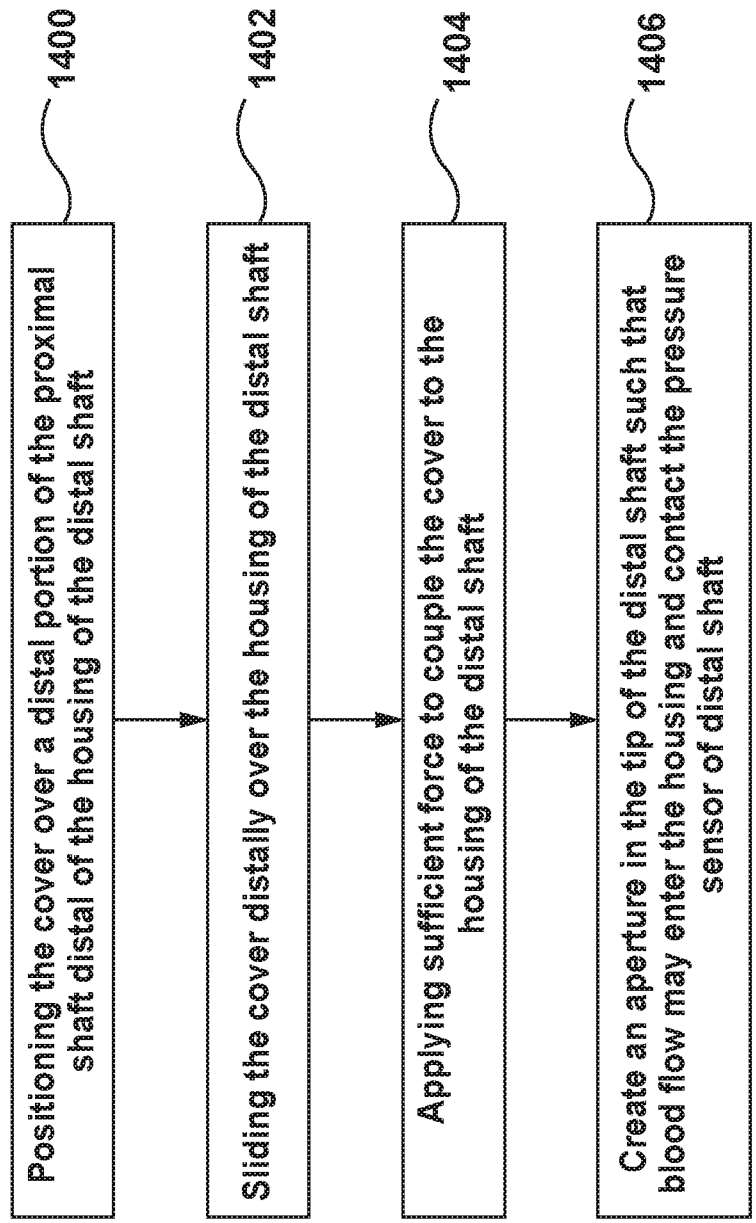
FIG. 14 is a block diagram of a method for manufacturing the distal shaft of FIG. 3 according to an embodiment hereof.

Referring to FIG. 14, a method of manufacturing a distal shaft 110 of an FFR catheter for measuring a distal pressure measurement on a distal side of a stenosis according to an embodiment hereof is described. Steps 1400-1406 of FIG. 14 reference the cover 132 and the distal shaft 110 components shown in FIGS. 3-5. The cover 132 of FIGS. 3-5 includes the cover lumen 154 configured to receive the housing 108 of the distal shaft 110 therein.

In step 1400, the cover 132 is positioned over the proximal shaft 112 proximal of the housing 108 of the distal shaft 110.

In step 1402, a sufficient force is applied distally to the cover 132 to distally slide or translate the cover 132 over the housing 108 of the distal shaft 110.

In step 1404, the force is applied distally to the cover 132 such that the coupling mechanism of the distal shaft 110 is engaged and the cover 132 is coupled to the housing 108 of the distal shaft 110.

In step 1406, the aperture 146 is created in the tip 134 extending from an outer surface of the tip 134 to the open seat 128 of the housing 108.

The method of FIG. 14 describes step 1404 as engaging at least one coupling mechanism. The step 1204 may include engaging a snap-fit coupling mechanism, a friction-fit coupling mechanism, an adhesive coupling mechanism, or any other coupling mechanism suitable for the purposes described herein. Moreover, the various coupling mechanisms described may be used in any combination. Further, in embodiments utilizing an adhesive coupling mechanism, the adhesive may be applied to the housing 108 and/or to the cover 132 at any time prior to step 1402.

Although the method of FIG. 14 describes step 1406 as occurring after steps 1400-1404, step 1406 may occur at any time during the manufacturing process, including being formed as part of the tip 134. Further, while step 1406 describes creating the aperture 146 in the tip 134, this is not meant to limit the method, and step 1406 may alternatively include creating the aperture 146 in a portion of the tip 134, in the cover 132, in a portion of the cover 132, or in any combination thereof. Even further, more than one aperture 146 may be created.

Figure 15:
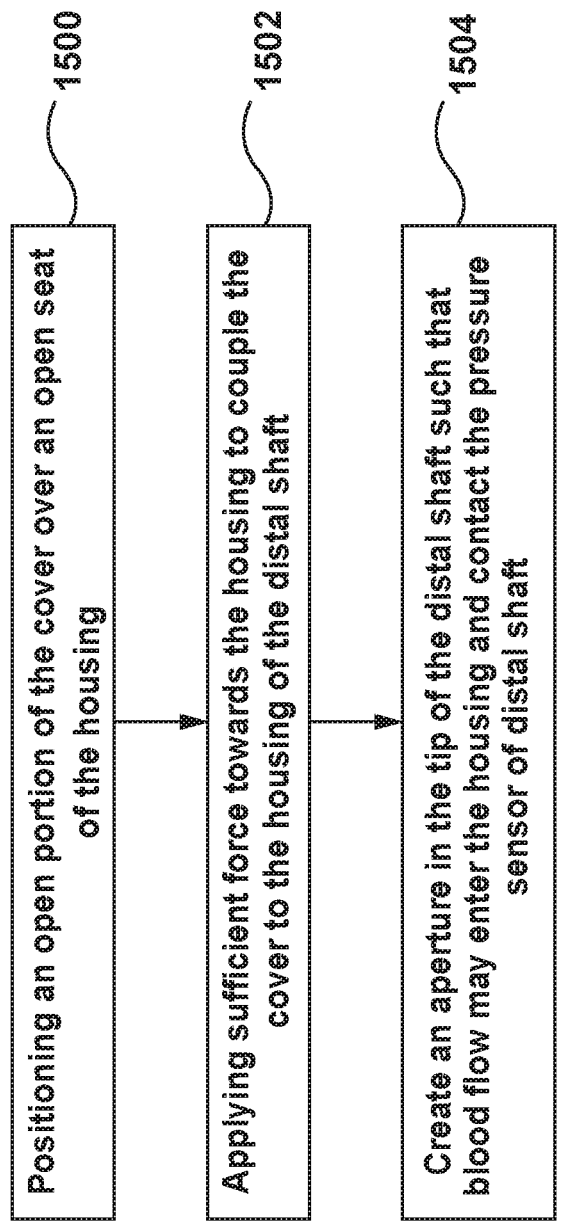
FIG. 15 is a block diagram of a method for manufacturing the distal shaft of FIG. 7 according to an embodiment hereof.

FIG. 15 shows a method of manufacturing a distal shaft 310 of an FFR catheter for measuring a distal pressure measurement on a distal side of a stenosis according to another embodiment hereof. Steps 1500-1504 of FIG. 15 reference the partial cylinder cover 332 and the distal shaft 310 shown in FIGS. 7-9.

In step 1500, the cover 332 is positioned with the open portion 355 of the cover 332 over the open seat 328 of the housing 308.

In step 1502, a sufficient force is applied to the cover 332 and/or the housing 308 towards each other such that the coupling mechanism is engaged and the cover 332 is coupled to the housing 308 of a distal shaft 310.

In step 1504, the aperture 346 is created in the tip 334 extending from an outer surface of the tip 334 to an open seat 328 of a housing 308.

The method of FIG. 15 describes step 1502 as engaging the coupling mechanism. Step 1502 may including engaging a friction-fit coupling mechanism, a snap-fit coupling mechanism, an adhesive coupling mechanism, or any other suitable coupling mechanism. Further, the various coupling mechanisms described may be used in any combination. If an adhesive coupling mechanism is utilized, the adhesive may be applied to the housing 308 and/or the cover 332 prior to step 1502.

Although the method of FIG. 15 describes step 1504 as occurring after steps 1500-1502, step 1504 may occur at any suitable time during the manufacturing method, including being formed as part of the tip 334.

Moreover while step 1504 describes creating the aperture 346 in the tip 334, this is not meant to limit the method, and step 1504 may alternatively include creating the aperture 346 in a portion of the tip 334, in the cover 332, in a portion of the cover 332, or in any combination thereof. Even further, more than one aperture 346 may be created.

While the methods of FIGS. 14-15 are described with respect to specific embodiments of the invention described herein, this is not meant to limit the methods, and persons skilled in the art will understand the methods described herein may utilize a cover according to other embodiments.

While only some embodiments according to the present invention have been described herein, it should be understood that they have been presented by way of illustration and example only, and not limitation. Various changes in form and detail can be made therein without departing from the spirit and scope of the invention. Further, each feature of each embodiment discussed herein, and of each reference cited herein, can be used in combination with the features of any other embodiment. All patents and publications discussed herein are incorporated by reference herein in their entirety.

What is claimed is:

1. A Fractional Flow Reserve (FFR) catheter comprising:
a distal shaft defining a housing, a guidewire lumen configured to receive a guidewire, the guidewire lumen extending through the housing, and a sensor wire lumen configured to receive pressure sensor wires;
a pressure sensor mounted in the housing;
a separate cover coupled to the housing and covering the pressure sensor, wherein the housing comprises a first material and the cover comprises a second material, wherein the second material is stiffer than the first material;
a tip coupled to a distal end of the housing, the tip including a tip lumen aligned with the guidewire lumen; and
an aperture disposed through the tip and/or the cover, the aperture configured to allow blood flow to the pressure sensor.

2. The catheter of claim 1, wherein the cover includes a proximal end and a distal end defining a cover lumen there between, wherein the housing is disposed within the cover lumen.

3. The catheter of claim 2, wherein the cover includes a coupling mechanism for coupling the cover to the housing.

4. The catheter of claim 3, wherein the coupling mechanism is a snap-fit mechanism including a first annular ring extending radially inwardly from an inside surface of the cover and a corresponding second annular ring extending radially outwardly from an outer surface of the housing.

5. The catheter of claim 3, wherein the coupling mechanism is a friction-fit mechanism such that a first portion of the cover includes a first inner diameter and a corresponding portion of the housing includes a second outer diameter, wherein the first inner diameter is smaller than the second outer diameter with the first portion of the cover not disposed over the portion of the housing, and wherein with the first portion of the cover disposed over the portion of the housing, the portion of the housing expands the first portion such that the cover is frictionally coupled to the housing.

6. The catheter of claim 3, wherein the coupling mechanism is an adhesive.

7. The catheter of claim 1,
wherein the cover includes a proximal end, a distal end, a first longitudinal edge, a second longitudinal edge, and a surface between the proximal end, the distal end, the first longitudinal edge, and the second longitudinal edge, the surface defining a partial cylinder with an open portion opposite the surface,
wherein the housing has an open seat in which the pressure sensor is disposed, and
wherein the open portion of the cover is aligned with the open seat of the housing such that the surface covers the open seat of the housing.

8. The catheter of claim 7, wherein the cover includes a coupling mechanism for coupling the cover to the housing.

9. The catheter of claim 8, wherein the coupling mechanism comprises a first protrusion extending inwardly from an inner surface of the cover adjacent the first longitudinal edge, a second protrusion extending inwardly from the inner surface of the cover adjacent the second longitudinal edge, a first channel corresponding to the first protrusion disposed in an outer surface of the housing adjacent the open seat of the housing, and a second channel corresponding to the second protrusion disposed in the outer surface of the housing adjacent the open seat of the housing, wherein the first protrusion is disposed in the first channel and the second protrusion is disposed in the second channel to couple the cover to the housing.

10. The catheter of claim 8, wherein the coupling mechanism comprises a first protrusion extending inwardly from an inner surface of the cover adjacent the first longitudinal edge, a second protrusion extending inwardly from the inner surface of the cover adjacent the second longitudinal edge, a third protrusion extending outwardly from an outer surface of the housing adjacent the open seat of the housing, and a fourth protrusion extending outwardly from the outer surface of the housing adjacent the open seat of the housing, wherein the first and the third protrusions overlap and the second and the fourth protrusions overlap to couple the cover to the housing.

11. The catheter of claim 8, wherein the coupling mechanism is an adhesive.

12. The catheter of claim 1, wherein the aperture is disposed in the tip.

13. The catheter of claim 12, wherein the aperture is shaped such that the aperture is generally parallel to a longitudinal axis of the housing.

14. The catheter of claim 12, wherein the aperture is configured to provide axial blood flow into a portion of the housing where the pressure sensor is housed.

15. The catheter of claim 1, wherein the housing includes a guidewire lumen and an open seat, wherein the pressure sensor is disposed in the open seat.

16. A method of manufacturing a distal shaft of an FFR catheter for measuring a distal pressure measurement on a distal side of a stenosis, the method comprising the steps of:
   positioning a separate cover at a housing of a distal shaft, the housing having a pressure sensor mounted therein, the distal shaft including a guidewire lumen for receiving a guidewire, the guidewire lumen extending through the housing, the housing comprising a first material and the cover comprising a second material, wherein the second material is stiffer than the first material;
   coupling the cover to the housing of the distal shaft to cover the pressure sensor; and
   providing an aperture through the cover and/or a portion of the distal shaft, wherein the aperture is configured to enable blood flow into the housing and into contact with the pressure sensor.

17. The method of claim 16, wherein the cover includes a lumen configured to receive the housing of the distal shaft therein, wherein the step of positioning the cover at the housing of the distal shaft comprises positioning the cover proximal to the housing and sliding the cover distally over the housing.

18. The method of claim 17, wherein the step of coupling the cover to the housing comprises frictionally coupling the cover to the housing.

19. The method of claim 16, wherein the cover comprises a partial cylinder, and wherein the step of positioning the cover at the housing of the distal shaft comprises positioning an open portion of the cover over an open seat of the housing.

20. The method of claim 16, wherein the step of coupling the cover to the housing comprises engaging at least one snap-fit mechanism.

21. The method of claim 16, wherein the step of coupling the cover to the housing comprises adhesively coupling the cover to the housing.

22. A Fractional Flow Reserve (FFR) catheter comprising:
   a distal shaft defining a housing, a guidewire lumen configured to receive a guidewire, the guidewire lumen extending through the housing, and a sensor wire lumen configured to receive pressure sensor wires;
   a pressure sensor mounted in the housing;
   a separate cover coupled to the housing and covering the pressure sensor, the separate cover coupled to the housing via a snap-fit mechanism including a first annular ring extending radially inwardly from an inside surface of the cover and a corresponding second annular ring extending radially outwardly from an outer surface of the housing;
   a tip coupled to a distal end of the housing, the tip including a tip lumen aligned with the guidewire lumen; and
   an aperture disposed through the tip and/or the cover, the aperture configured to allow blood flow to the pressure sensor.

23. The catheter of claim 22, wherein the snap-fit mechanism comprises a first protrusion extending inwardly from an inner surface of the cover adjacent a first longitudinal edge of the cover, a second protrusion extending inwardly from the inner surface of the cover adjacent a second longitudinal edge of the cover, a first channel corresponding to the first protrusion disposed in an outer surface of the housing adjacent an open seat of the housing, and a second channel corresponding to the second protrusion disposed in the outer surface of the housing adjacent the open seat of the housing, wherein the first protrusion is disposed in the first channel and the second protrusion is disposed in the second channel to couple the cover to the housing.

24. The catheter of claim 22, wherein the snap-fit mechanism comprises a first protrusion extending inwardly from an inner surface of the cover adjacent a first longitudinal edge of the cover, a second protrusion extending inwardly from the inner surface of the cover adjacent a second longitudinal edge of the cover, a third protrusion extending outwardly from an outer surface of the housing adjacent an open seat of the housing in which the pressure sensor is disposed, and a fourth protrusion extending outwardly from the outer surface of the housing adjacent the open seat of the housing, wherein the first and the third protrusions overlap and the second and the fourth protrusions overlap to couple the cover to the housing.

25. A Fractional Flow Reserve (FFR) catheter comprising:
   a distal shaft defining a housing, a guidewire lumen configured to receive a guidewire, the guidewire lumen extending through the housing, and a sensor wire lumen configured to receive pressure sensor wires;
   a pressure sensor mounted in the housing;
   a separate cover coupled to the housing and covering the pressure sensor; the cover being coupled to the housing via a friction-fit mechanism such that a first portion of the cover includes a first inner diameter and a corresponding portion of the housing includes a second outer diameter, wherein the first inner diameter is smaller than the second outer diameter with the first portion of the cover not disposed over the portion of the housing, and wherein with the first portion of the cover disposed over the portion of the housing, the portion of the housing expands the first portion such that the cover is frictionally coupled to the housing;
   a tip coupled to a distal end of the housing, the tip including a tip lumen aligned with the guidewire lumen; and
   an aperture disposed through the tip and/or the cover, the aperture configured to allow blood flow to the pressure sensor.

* * * * *